(12) United States Patent
Tsai et al.

(10) Patent No.: US 11,339,408 B2
(45) Date of Patent: May 24, 2022

(54) NUCLEASE WITH ENHANCED EFFICIENCY OF GENOME EDITING

(71) Applicant: APPLIED STEMCELL, INC., Milpitas, CA (US)

(72) Inventors: Ruby Yanru Tsai, San Jose, CA (US); Ling-jie Kong, Foster City, CA (US); Jingyuan Cao, San Jose, CA (US)

(73) Assignee: APPLIED STEMCELL, INC., Milpitas, CA (US)

( * ) Notice: Subject to any disclaimer, the term of this patent is extended or adjusted under 35 U.S.C. 154(b) by 285 days.

(21) Appl. No.: 15/754,589

(22) PCT Filed: Aug. 22, 2016

(86) PCT No.: PCT/US2016/047937
§ 371 (c)(1),
(2) Date: Feb. 22, 2018

(87) PCT Pub. No.: WO2017/031483
PCT Pub. Date: Feb. 23, 2017

(65) Prior Publication Data
US 2018/0216135 A1 Aug. 2, 2018

Related U.S. Application Data

(60) Provisional application No. 62/207,860, filed on Aug. 20, 2015.

(51) Int. Cl.
| | |
|---|---|
| *C12N 9/22* | (2006.01) |
| *C12N 15/113* | (2010.01) |
| *C12N 15/63* | (2006.01) |
| *C12N 15/90* | (2006.01) |
| *C12N 15/11* | (2006.01) |

(52) U.S. Cl.
CPC ............ *C12N 15/907* (2013.01); *C12N 9/22* (2013.01); *C12N 15/111* (2013.01); *C12N 15/113* (2013.01); *C12N 15/63* (2013.01); *C07K 2319/00* (2013.01); *C07K 2319/80* (2013.01); *C07K 2319/81* (2013.01); *C12N 2310/10* (2013.01); *C12N 2310/20* (2017.05)

(58) Field of Classification Search
None
See application file for complete search history.

(56) References Cited

U.S. PATENT DOCUMENTS

| | | |
|---|---|---|
| 2015/0071899 A1 | 3/2015 | Liu et al. |
| 2015/0166980 A1 | 6/2015 | Liu et al. |
| 2015/0218573 A1 | 8/2015 | Loque et al. |
| 2016/0177278 A1* | 6/2016 | Wolfe ............... C12N 9/22 435/199 |

FOREIGN PATENT DOCUMENTS

| | | |
|---|---|---|
| CN | 103930550 A | 7/2014 |
| CN | 104781404 A | 7/2015 |
| EP | 2796558 A1 | 10/2014 |
| WO | 2015-073867 A1 | 5/2015 |

OTHER PUBLICATIONS

Dong et al. Stable Gene Silencing in Zebrafish with Spatioetemporally Targetable RNA Interference. Apr. 2013. Genetics. vol. 193, pp. 1065-1071. (Year: 2013).*
Xue et al. CRISPR/Cas9 Mediates Efficient Conditional Mutagenesis in *Drosophilia*. Published online Sep. 5, 2014. G3. vol. 4, No. 11, pp. 2167-2173. (Year: 2014).*
Jinek, Martin et al., "A programmable dual-RNA-guided DNA endonuclease in adaptive bacterial immunity", Science, 2012, vol. 337, pp. 816-821.
The International Search Report and Written Opinion for PCT/US2016/047937.
Search report of the First Office Action for Chinese Patent Application No. 201680048134.8, dated Aug. 4, 2020.

* cited by examiner

*Primary Examiner* — Channing S Mahatan
(74) *Attorney, Agent, or Firm* — Jun He Law Offices P.C.; Yi Zhang

(57) ABSTRACT

The present disclosure provides a composition comprising a site-specific nuclease domain capable of cleaving a target DNA sequence; and a sequence-specific DNA binding domain capable of specifically binding to a recognition DNA sequence, wherein the site-specific nuclease domain operably links to the sequence-specific DNA binding domain.

9 Claims, 1 Drawing Sheet
Specification includes a Sequence Listing.

SEQUENCE LISTING

```
<160> NUMBER OF SEQ ID NOS: 20

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255
```

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

-continued

```
Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
```

| | | | | | | | | | | |
|---|---|---|---|---|---|---|---|---|---|---|
| | | 1085 | | | | 1090 | | | 1095 | |
| Glu | Val | Gln | Thr | Gly | Gly | Phe | Ser | Lys | Glu | Ser | Ile | Leu | Pro | Lys |
| | 1100 | | | | 1105 | | | | 1110 | |

Arg Asn Ser Asp Lys Leu Ile Ala Arg Lys Lys Asp Trp Asp Pro
   1115                1120                1125

Lys Lys Tyr Gly Gly Phe Asp Ser Pro Thr Val Ala Tyr Ser Val
   1130                1135                1140

Leu Val Val Ala Lys Val Glu Lys Gly Lys Ser Lys Lys Leu Lys
   1145                1150                1155

Ser Val Lys Glu Leu Leu Gly Ile Thr Ile Met Glu Arg Ser Ser
   1160                1165                1170

Phe Glu Lys Asn Pro Ile Asp Phe Leu Glu Ala Lys Gly Tyr Lys
   1175                1180                1185

Glu Val Lys Lys Asp Leu Ile Ile Lys Leu Pro Lys Tyr Ser Leu
   1190                1195                1200

Phe Glu Leu Glu Asn Gly Arg Lys Arg Met Leu Ala Ser Ala Gly
   1205                1210                1215

Glu Leu Gln Lys Gly Asn Glu Leu Ala Leu Pro Ser Lys Tyr Val
   1220                1225                1230

Asn Phe Leu Tyr Leu Ala Ser His Tyr Glu Lys Leu Lys Gly Ser
   1235                1240                1245

Pro Glu Asp Asn Glu Gln Lys Gln Leu Phe Val Glu Gln His Lys
   1250                1255                1260

His Tyr Leu Asp Glu Ile Ile Glu Gln Ile Ser Glu Phe Ser Lys
   1265                1270                1275

Arg Val Ile Leu Ala Asp Ala Asn Leu Asp Lys Val Leu Ser Ala
   1280                1285                1290

Tyr Asn Lys His Arg Asp Lys Pro Ile Arg Glu Gln Ala Glu Asn
   1295                1300                1305

Ile Ile His Leu Phe Thr Leu Thr Asn Leu Gly Ala Pro Ala Ala
   1310                1315                1320

Phe Lys Tyr Phe Asp Thr Thr Ile Asp Arg Lys Arg Tyr Thr Ser
   1325                1330                1335

Thr Lys Glu Val Leu Asp Ala Thr Leu Ile His Gln Ser Ile Thr
   1340                1345                1350

Gly Leu Tyr Glu Thr Arg Ile Asp Leu Ser Gln Leu Gly Gly Asp
   1355                1360                1365

<210> SEQ ID NO 2
<211> LENGTH: 4104
<212> TYPE: DNA
<213> ORGANISM: Artificial Sequence
<220> FEATURE:
<223> OTHER INFORMATION: Synthetic

<400> SEQUENCE: 2
atggacaaga agtatagcat cgggctggac attggaacga actcggttgg ttgggctgtg     60
attacggacg aatacaaggt gccatccaag aagtttaagg tcctgggaaa caccgaccgt    120
cactcaatca agaagaatct cattggagcc ctgctcttcg atagtgggga gaccgccgaa    180
gctactcgac tgaagcgaac ggctcgccgg cgttatacac gacgcaagaa tcgcatctgc    240
tacctccagg agattttcag caacgaaatg gctaaggttg atgactcatt ctttcatcga    300
ctcgaagaaa gtttcttggt cgaggaggat aagaagcacg agcgccatcc gatctttggt    360
aacattgtgg atgaggttgc ctatcacgaa aagtacccaa ctatctatca tcttcgtaag    420

```
aagctggtcg atagcacgga caaggctgat ttgcgactta tctacctggc actcgcgcac    480
atgattaagt tccgcggcca ttttcttatc gagggtgacc tgaacccgga taattctgac    540
gttgataagc tcttcatcca gttggtccaa acctacaatc agctgtttga ggaaaaccct    600
attaatgcat ctggcgtgga cgccaaggct atcctttcgg cgcgcctgtc taagtcgcgg    660
cgtttggaga accttatcgc acaactcccc ggcgaaaaga gaacggcct  cttcggtaat    720 ttgattgcgt tgtcacttgg tctgactcct aacttcaaga gtaattttga cctggcagag    780
gatgcgaagc tccagttgtc taaggatacg tatgatgacg atctcgacaa cttgcttgcc    840
caaatcggtg accagtacgc tgatcttttc ctggccgcta agaatctctc agatgcaatc    900
ctgctcagtg acattttgcg ggtcaacacc gagattacta aggcccccct gtcagctagt    960
atgatcaagg gtatgatga  gcaccatcag gacctcacct tgcttaaggc cctcgtgcgt   1020
cagcaattgc ctgagaagta caaggaaatc ttctttgacc aatccaagaa cggatacgca   1080
gggtatattg atggcggtgc gagccaggag gaattctaca agtttatcaa gccgattttg   1140
gagaagatgg acggcactga ggaactgctc gtcaagctga atcgcgaaga tttgcttcgt   1200
aagcaacgaa cgttcgacaa cggctccatc ccgcaccaga ttcatctggg cgagctccac   1260
gccatccttc gacgccagga agatttctac ccatttctga aggacaaccg tgagaagatc   1320
gaaaagattc ttacattccg aatccctac  tatgtgggac cttggcccg  tgggaattcc   1380 cgatttgctt ggatgacccg aaagagcgag gaaaccatca ctccgtggaa cttcgaggaa   1440
gtcgtggaca agggtgcatc cgcgcagagc ttcattgagc ggatgaccaa ttttgataag   1500
aaccttccga atgaaaaggt cctgccaaag cattcgctgc tctacgagta tttcaccgtg   1560
tataacgaac tgactaaggt caagtacgtg acggagggaa tgcggaagcc agccttcctc   1620
tcaggggaac aaaagaaggc tatcgtcgat ttgcttttta agaccaatcg taaagtgact   1680
gttaagcagc tgaaggagga ttatttcaag aagattgaat gtttcgactc cgtcgagatc   1740
agcggcgtgg aagatcgctt taacgcttcc ctcggtacct accacgacct gctcaagatc   1800
attaaggaca aggatttcct cgataacgag gaaaatgagg acatcttgga agatattgtc   1860
ctcacgttga cactttttga ggaccgcgaa atgatcgagg aacggctcaa gacatatgcc   1920
catttgttcg acgataaggt gatgaagcag ctgaagcggc gtcgatacac cggatggggt   1980
cgccttagcc ggaagctgat caacggcatt cgagataagc aatctggtaa gactatcttg   2040
gatttcctta agtcggacgg cttcgccaac cgcaatttta tgcagcttat tcacgacgat   2100
tccctgacgt tcaaggagga catccagaag gcacaagtct caggacaagg ggattccctg   2160
cacgagcata tcgccaacct ggctggatcc ccggcgatca agaagggat  tcttcagacc   2220 gtcaaggttg tcgacgagct ggtcaaggtg atgggccgtc ataagccaga aaacatcgtg   2280
attgagatgg cccgagaaaa tcagaccact caaaagggtc agaagaacag ccgcgagcgg   2340
atgaagcgga tcgaggaagg cattaaggaa cttggttctc agatcctgaa ggagcaccct   2400
gttgaaaaca cacagctcca aaatgagaag ctgtatctct actatttgca aaatggacgc   2460
gacatgtacg tcgatcagga gctcgacatt aaccggttgt cggactacga tgttgaccat   2520
atcgtcccgc aatccttcct taaggacgat agcattgata caaggtgct  gactcgctca   2580 gataagaacc ggggcaagtc cgacaatgtt ccaagcgagg aagtggttaa gaagatgaag   2640
aactactggc gccaattgct taatgccaag ctcatcacac agcgcaagtt tgacaacttg   2700
accaaggccg agcggggagg gctgagtgaa ctcgataagg ctggcttcat caagcgtcaa   2760
```

```
ctcgtggaga cgcgacagat cacaaagcac gttgctcaga ttctggactc ccggatgaac    2820
acaaagtacg acgagaatga taagctcatc cgtgaagtta aggtcattac cctcaagtct    2880
aagttggtgt cggatttccg caaggacttc caattttata aggttcggga gatcaacaat    2940
tatcaccatg cacatgatgc gtacctcaac gcagtcgtgg gaactgcgct catcaagaag    3000
tatcccaagt tggagtccga attcgtctac ggggattata aggtttacga cgtccgcaag    3060
atgatcgcca agagtgagca ggaaattggc aaggccacgg ctaagtattt cttttactcc    3120
aacatcatga atttctttaa gacggagatc acactcgcca atggagaaat ccgtaagcga    3180
cctttgattg agaccaacgg cgagactggt gaaatcgttt gggataaggg cgcgacttc    3240
gctaccgtgc ggaaggttct gagcatgccg caagtcaata tcgtcaagaa aaccgaggtg    3300
cagacaggcg gtttctctaa ggaatcgatt cttccaaagc gtaactctga caagctgatc    3360
gctcgaaaga aggattggga ccccaagaag tatggagggt tcgattctcc tacagtggca    3420
tactcggttc tcgttgtcgc gaaggttgag aagggaaagt ctaagaagct gaagtcggtc    3480
aaggaactgc tcgggatcac cattatggag cgctccagct tcgaaaagaa tcccatcgac    3540
tttctcgagg ccaagggcta taaggaagtc aagaaggatc ttatcattaa gctgcctaag    3600
tactctttgt tcgagcttga aaacggtcga agcgaatgc tcgcatcggc aggagagttg    3660
cagaagggga atgaattggc acttccctca aagtacgtga acttcctgta tctcgcgtcc    3720
cactacgaga agctgaaggg tagccctgag gacaacgaac agaagcaact ttttgttgag    3780
caacacaagc attatctgga tgagatcatt gaacagattt cagagttcag taagcgcgtc    3840
atcctcgccg atgctaatct cgacaagtgt tgtcggcct acaacaagca ccgtgacaag    3900
ccgatccgag agcaggctga aaatatcatt catctgttca ccctcactaa cttgggagca    3960
ccagcagcgt tcaagtattt tgatacgaca atcgaccgta agcgatacac gtccacaaag    4020
gaggtgcttg atgcgacccct gattcatcaa tccatcactg ggctctatga aacccgtatc    4080
gaccttagtc aactgggggg cgac                                          4104

<210> SEQ ID NO 3
<211> LENGTH: 34
<212> TYPE: PRT
<213> ORGANISM: Artificial Sequence
<220> FEATURE:
<223> OTHER INFORMATION: Synthetic

<400> SEQUENCE: 3

Leu Thr Pro Glu Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 4
<211> LENGTH: 35
<212> TYPE: PRT
<213> ORGANISM: Artificial Sequence
<220> FEATURE:
<223> OTHER INFORMATION: Synthetic

<400> SEQUENCE: 4

Leu Thr Pro Glu Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30
```

Pro His Asp
      35

<210> SEQ ID NO 5
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Zinc finger domain component
<220> FEATURE:
<221> NAME/KEY: misc_feature
<222> LOCATION: (2)..(3)
<223> OTHER INFORMATION: Xaa can be any amino acid or no amino acid
<220> FEATURE:
<221> NAME/KEY: misc_feature
<222> LOCATION: (4)..(5)
<223> OTHER INFORMATION: Xaa can be any amino acid or no amino acid
<220> FEATURE:
<221> NAME/KEY: misc_feature
<222> LOCATION: (7)..(18)
<223> OTHER INFORMATION: Xaa can be any amino acid
<220> FEATURE:
<221> NAME/KEY: misc_feature
<222> LOCATION: (20)..(22)
<223> OTHER INFORMATION: Xaa can be any amino acid
<220> FEATURE:
<221> NAME/KEY: misc_feature
<222> LOCATION: (23)..(24)
<223> OTHER INFORMATION: Xaa can be any amino acid or no amino acid

<400> SEQUENCE: 5

Cys Xaa Xaa Xaa Xaa Cys Xaa Xaa Xaa Xaa Xaa Xaa Xaa Xaa Xaa Xaa
1               5                   10                  15

Xaa Xaa His Xaa Xaa Xaa Xaa Xaa His
            20                  25

<210> SEQ ID NO 6
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: Xaa can be any amino acid
<220> FEATURE:
<221> NAME/KEY: misc_feature
<222> LOCATION: (4)..(4)
<223> OTHER INFORMATION: Xaa can be a hydrophobic amino acid
<220> FEATURE:
<221> NAME/KEY: misc_feature
<222> LOCATION: (5)..(7)
<223> OTHER INFORMATION: Xaa can be any amino acid
<220> FEATURE:
<221> NAME/KEY: misc_feature
<222> LOCATION: (8)..(8)
<223> OTHER INFORMATION: Xaa can be a hydrophobic amino acid
<220> FEATURE:
<221> NAME/KEY: misc_feature
<222> LOCATION: (9)..(9)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa can be a hydrophobic amino acid
<220> FEATURE:
<221> NAME/KEY: misc_feature
<222> LOCATION: (11)..(14)
<223> OTHER INFORMATION: Xaa can be any amino acid
<220> FEATURE:

```
<221> NAME/KEY: misc_feature
<222> LOCATION: (15)..(15)
<223> OTHER INFORMATION: Xaa can be a hydrophobic amino acid
<220> FEATURE:
<221> NAME/KEY: misc_feature
<222> LOCATION: (16)..(17)
<223> OTHER INFORMATION: Xaa can be any amino acid
<220> FEATURE:
<221> NAME/KEY: misc_feature
<222> LOCATION: (18)..(18)
<223> OTHER INFORMATION: Xaa can be a hydrophobic amino acid
<220> FEATURE:
<221> NAME/KEY: misc_feature
<222> LOCATION: (19)..(20)
<223> OTHER INFORMATION: Xaa can be any amino acid

<400> SEQUENCE: 6

Xaa Xaa Xaa Xaa Ala Xaa Xaa Xaa Gly Xaa Xaa Xaa Xaa Xaa Xaa
1               5                   10                  15

Xaa Xaa Xaa Xaa
            20

<210> SEQ ID NO 7
<211> LENGTH: 147
<212> TYPE: PRT
<213> ORGANISM: Artificial Sequence
<220> FEATURE:
<223> OTHER INFORMATION: Synthetic

<400> SEQUENCE: 7

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Asn Lys Gly Gln Arg Gln Leu
    130                 135                 140

Thr Val Ser
145

<210> SEQ ID NO 8
<211> LENGTH: 441
<212> TYPE: DNA
<213> ORGANISM: Artificial Sequence
<220> FEATURE:
<223> OTHER INFORMATION: Synthetic

<400> SEQUENCE: 8
atgaagctac tgtcttctat cgaacaagca tgcgatattt gccgacttaa aaagctcaag      60
tgctccaaag aaaaaccgaa gtgcgccaag tgtctgaaga caactgggga gtgtcgctac     120
tctcccaaaa ccaaaaggtc tccgctgact agggcacatc tgacagaagt ggaatcaagg     180
```

```
ctagaaagac tggaacagct atttctactg attttttcctc gagaagacct tgacatgatt      240
ttgaaaatgg attctttaca ggatataaaa gcattgttaa caggattatt tgtgcaagat      300
aatgtgaata aagatgccgt cacagataga ttggcttcag tggagactga tatgcctcta      360
acattgagac agcatagaat aagtgcgaca tcatcatcgg aagagagtag taacaaaggt      420
caaagacagt tgactgtatc g                                                441

<210> SEQ ID NO 9
<211> LENGTH: 93
<212> TYPE: DNA
<213> ORGANISM: Artificial Sequence
<220> FEATURE:
<223> OTHER INFORMATION: Synthetic

<400> SEQUENCE: 9
cggagtactg tcctccgagc ggagtactgt cctccgagcg gagtactgtc ctccgagcgg      60
agtactgtcc tccgagcgga gtactgtcct ccg                                   93

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
agtcgcttct cgattatggg                                                  20

<210> SEQ ID NO 11
<211> LENGTH: 60
<212> TYPE: DNA
<213> ORGANISM: Artificial Sequence
<220> FEATURE:
<223> OTHER INFORMATION: Synthetic

<400> SEQUENCE: 11
tcgacggcgc gtaaccggta agtaagggcg aattccagca cactggcggc cgttactagt      60

<210> SEQ ID NO 12
<211> LENGTH: 2000
<212> TYPE: DNA
<213> ORGANISM: Artificial Sequence
<220> FEATURE:
<223> OTHER INFORMATION: Synthetic

<400> SEQUENCE: 12
ggtttgttgg acttagcttt cagctaaata tataataaat aaaacaaaac aagcagttaa      60
atgaaatgta atgggccaga gagcttcagc ttttatttcc ttactgctca gtaaaaagag      120
aaaaccatca atgtccacgt attctgtaat ccacagaaca agtccggggc tacagctata      180
ctgtccacag ttgcaattca aattagataa aaaataaaaa ttcagttctt tagtcatacc      240
agccactttt ccaatgctca agattaataa aatgtcaaac cataaagaca tttacatgtc      300
gctcactcca tttacttaaa gttggctaga catcagagta tactaggagc tcaggagtac      360
aagacactat tccttcaaaa agctcagaat agttaaggta atttaaatca gcaatgacaa      420
caaccccaga attactatga cccacgcagt acaaactgct caggagtcag aagaaaactg      480 ctttttttaaa agggcagttt gggtcataga acaacagacc atggaaggca tgaccaaagg      540
ggagatgaca tttgaatctg caggattaaa agcagcaagg gtagcattcc aaaaagaacc      600
```

```
acccccacaaa gatatatgac gtctctatga tttgggtaac tgcaattcat tccatgtgac    660
ttcaggagag aggtcatatt tgtgtgtgta gtatgtggaa atagtgaaa  atgaaaaag     720
ctgttaaatt gaggaaagtc tatccaggga ccttatgcat cacattcacg agaacagaat    780
tcatcctgta aaccaggggt gtccaatctt tcggcttccc tgggccacac tgcaagaact    840
gtcttgggcc acatataaag gacagctgat gagcaaaaaa aaaaaacaga caacaacaac    900
aaaaaaaaca ccccgcaaaa aaaactccta aactttaag  aaagtttacg aatttgtgtt    960
gggtcgcatt caagctgtc  ctgggtccca tgcggcccgc gggttagaca acttgctgta   1020
aacagtacaa gccagtaatg gagtttcacc tgtcattttc atgctctatc ttccttaggg  1080
acaatcatcc taacaagatg taagatggat caaaagataa cactaaagac agagacagca  1140
atttggaagc tatcacacag gcatctgaga tcagttacta actggtaaga acagaaatga  1200
gaggtattta gaggaagaaa aagggagatg ttgcctaacc tcagatccaa ttctctgtaa  1260
agcagtagtc aagatcacct ggactgtgaa gacggtcagg gacagaatcc cagctaagga  1320
aaaaggataa aatgaaaatc aagataaaca tttaagaacg tgaactaggg aggaataaaa  1380
gcactgctgg gtaagagtca agccccagct caagccttaa tttgtggtgg aaccaatctg  1440
tctggtttcg cgagacacca ggctacccaa gatcaagaga gggagaaagc tagtgctatg  1500
tctgaatact agaggagcaa gtacaacaaa tggaaaatgg gatcaagtat gagtgagagt  1560
tgctaagatg cctggtaggg atgcaaaggg gtagagagcc tggggagaga gggtgaggga  1620
gggaagcact ggtttctcaa gcaaaagcta aatttttct  attaagattt aacctgatgc  1680
tacactttgg tggtgcagca agggtctcaa atggtataaa actcaggtga tcatgcttta  1740
tgtctgtctc tagaaaaatg ctccaaaaat gataagtagt gataatccgc agtctcgttg  1800
cataaaatca gccccaggtg aatgactaag ctccatttcc ctaccccacc cttattacaa  1860
taacctcgac accaactcta gtccgtggga agataaacta atcggagtcg cccctcaaat  1920
cttacagctg ctcactcccc tgcagggcaa cgcccaggga ccaagttagc cccttaagcc  1980
taggcaaaag aatcccgccc                                               2000
```

<210> SEQ ID NO 13
<211> LENGTH: 1744
<212> TYPE: DNA
<213> ORGANISM: Artificial Sequence
<220> FEATURE:
<223> OTHER INFORMATION: Synthetic

<400> SEQUENCE: 13

```
ataatcgaga agcgactcga catggaggcg atgacgagat cacgcgagga ggaaaggagg    60
gagggcttct tccaggccca gggcggtcct tacaagacgg gaggcagcag agaactccca   120
taaaggtatt gcggcactcc cctcccctg  cccagaaggg tgcggccttc tctccacctc   180
ctccaccgca gctccctcag gattgcagct cgcgccggtt tttggagaac aagcgcctcc   240
cacccacaaa ccagccggac cgaccccgc  tcctccccca ccccacgag  tgcctgtagc   300
aggtcgggct tgtctcgccc ttcaggcggt gggaacccgg ggcggagccg cggccgccgc   360
catccagaag tctcggccgg cagcccgccc ccgcctccag cgcgcgcttc ctgccacgtt   420
gcgcaggggc gcggggccag acactgcggc gctcggcctc ggggaggacc gtaccaacgc   480
ccgcctcccc gccaccccg  cgcccgcgc  agtggtttcg ctcatgtgag actcgagcca   540
gtagcaaggg cccggtccca cagcttcgac agccaatcag gtgtcgaaga caagcaggcg   600
gcgggtaaac cgactccccc gaaggaaggg gagggtggga ggacgcccgc gccagagccg   660
```

```
atttcactga ccctccccct ccgccgcagg aggccggccg cgcccgcaca cccagcatct    720
ctacacccca cctacctacc cgccccaccc aggggggcaac gcgagagtcg ctaagcggct    780
gcgtactccc gacggcgtaa ctgacaggag ctttactcca accagaatac gccatttgtg    840
ttttcacaca cggcgggagg agaaacggcc aatcggcgac aagaggctag ccggaagcgc    900
tcctccctct gcgagagcaa tggctccgtc cggtttcgag catttccgc tcccttctcc     960 ctccccctcc ggttgccgca gggcgggcct ccctcccgcc tgcatccagc cacccctttc   1020
cctcccaacg taacaaacat tatgttcccg acttcccacg ggaaaggcaa ccccccgcaag  1080 ccaccagacg gccccctag ccacccatcc ccccagtgta ccgcacctcc cctcccacca    1140
gagttccgct cccctaccta gccgaggctc tctgaggagc cggagcgccg aagcacagcc   1200
tcttctctag gcgccccgg cggcttccgc tgattggcgg cgagtgggcc aatgggtgcg    1260
gggcggtggg cggagaggcc aatggcgcgg cgggaggggg cgtgtcccgg gtgcccctgg   1320
cgccggcgct gggaatcccc gtgcggtcag tggcgtttcc gctcgggcag cgggctgagt   1380
gagctgccgc cgccgccgcc gccgccgccg ccgccgccgc tgccggggga ggggcggccg   1440
ccgcccgcct gcgctcagag actcacgcag ccccagtccc gccagtccgc caacacagta   1500
gtgccggccc ccctctttcc ctggccctgc ccccctccc cgcctttggc tcgctccgcc    1560
tttctgcccc ccaccccac ctcacgggta cgggccattc ccggccagga aacgccgtgg    1620
cgccgcgttg ggcctaactc gagtcctgcc gcctcccggg agtgccgtgc ccgcagccc    1680 gggcccaggc cccggcagcg cctgggacaa ggtaagggtc cgacagaaaa gagaccgaac   1740
ctca                                                                1744
```

<210> SEQ ID NO 14
<211> LENGTH: 4758
<212> TYPE: DNA
<213> ORGANISM: Artificial Sequence
<220> FEATURE:
<223> OTHER INFORMATION: Synthetic

<400> SEQUENCE: 14

```
atggactata aggaccacga cggagactac aaggatcatg atattgatta caaagacgat     60
gacgataaga tggcccccaa agaagaagcgg aaggtcggta tccacggagt cccagcagcc   120
gacaagaagt acagcatcgg cctggacatc ggcaccaact ctgtgggctg ggccgtgatc   180
accgacgagt acaaggtgcc cagcaagaaa ttcaaggtgc tgggcaacac cgaccggcac   240
agcatcaaga gaacctgat cggagccctg ctgttcgaca cggcgaaac agccgaggcc    300 acccggctga agagaaccgc cagaagaaga taccagac ggaagaaccg gatctgctat    360
ctgcaagaga tcttcagcaa cgagatggcc aaggtggacg acagcttctt ccacagactg    420
gaagagtcct tcctggtgga agaggataag aagcacgagc ggcacccat cttcggcaac    480 atcgtggacg aggtggccta ccacgagaag taccccacca tctaccacct gagaaagaaa   540
ctggtggaca gcaccgacaa ggccgacctg cggctgatct atctggccct ggcccacatg   600
atcaagttcc ggggccactt cctgatcgag ggcgacctga accccgacaa cagcgacgtg    660
gacaagctgt tcatccagct ggtgcagacc tacaaccagc tgttcgagga aaaccccatc    720
aacgccagcg gcgtggacgc caaggccatc ctgtctgcca gactgagcaa gagcagacgg    780
ctggaaaatc tgatcgccca gctgcccggc gagaagaaga tggcctgtt cggaaacctg    840 attgccctga gcctgggcct gacccccaac ttcaagagca acttcgacct ggccgaggat    900
```

```
gccaaactgc agctgagcaa ggacacctac gacgacgacc tggacaacct gctggcccag    960
atcggcgacc agtacgccga cctgtttctg gccgccaaga acctgtccga cgccatcctg   1020
ctgagcgaca tcctgagagt gaacaccgag atcaccaagg ccccctgag cgcctctatg    1080
atcaagagat acgacgagca ccaccaggac ctgaccctgc tgaaagctct cgtgcggcag   1140
cagctgcctg agaagtacaa agagattttc ttcgaccaga gcaagaacgg ctacgccggc   1200
tacattgacg gcggagccag ccaggaagag ttctacaagt tcatcaagcc catcctggaa   1260
aagatggacg gcaccgagga actgctcgtg aagctgaaca gagaggacct gctgcggaag   1320
cagcggaccc tcgacaacgg cagcatcccc accagatcc acctgggaga gctgcacgcc    1380
attctgcggc ggcaggaaga tttttaccca ttcctgaagg acaaccggga aaagatcgag   1440
aagatcctga ccttccgcat cccctactac gtgggcccte tggccagggg aaacagcaga   1500
ttcgcctgga tgaccagaaa gagcgaggaa accatcaccc cctggaactt cgaggaagtg   1560
gtggacaagg gcgcttccgc ccagagcttc atcgagcgga tgaccaactt cgataagaac   1620
ctgcccaacg agaaggtgct gcccaagcac agcctgctgt acgagtactt caccgtgtat   1680
aacgagctga ccaaagtgaa atacgtgacc gagggaatga gaaagcccgc cttcctgagc   1740
ggcgagcaga aaaaggccat cgtggacctg ctgttcaaga ccaaccggaa agtgaccgtg   1800
aagcagctga agaggactta cttcaagaaa atcgagtgct tcgactccgt ggaaatctcc   1860
ggcgtggaag atcggttcaa cgcctccctg ggcacatacc acgatctgct gaaaattatc   1920
aaggacaagg acttcctgga caatgaggaa aacgaggaca ttctggaaga tatcgtgctg   1980
accctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga gctgatcaa cggcatccgg gacaagcagt ccggcaagac aatcctggat   2160
ttcctgaagt ccgacggctt cgccaacaga aacttcatgc agctgatcca cgacgacagc   2220
ctgacctta aagaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca gcccgagaa catcgtgatc   2400
gaaatggcca gagagaacca gaccacccag aagggacaga agaacagccg cgagagaatg   2460
aagcggatcg aagagggcat caaagagctg ggcagccaga tcctgaaaga acaccccgtg   2520
gaaaacaccc agctgcagaa cgagaagctg tacctgtact acctgcagaa tgggcgggat   2580
atgtacgtgg accaggaact ggacatcaac cggctgtccg actacgatgt ggaccatatc   2640
gtgcctcaga gctttctgaa ggacgactcc atcgacaaca aggtgctgac cagaagcgac   2700
aagaaccggg gcaagagcga caacgtgccc tccgaagagg tcgtgaagaa gatgaagaac   2760
tactggcggc agctgctgaa cgccaagctg attacccaga gaaagttcga caatctgacc   2820
aaggccgaga aggcggcct gagcgaactg gataaggccg gcttcatcaa gagacagctg   2880
gtggaaaccc ggcagatcac aaagcacgtg gcacagatcc tggactcccg gatgaacact   2940
aagtacgacg agaatgacaa gctgatccgg gaagtgaaag tgatcaccct gaagtccaag   3000
ctggtgtccg atttccggaa ggatttccag ttttacaaag tgcgcgagat caacaactac   3060
caccacgccc acgacgccta cctgaacgcc gtcgtgggaa ccgccctgat caaaaagtac   3120
cctaagctgg aaagcgagtt cgtgtacggc gactacaagg tgtacgacgt gcggaagatg   3180
atcgccaaga gcgagcagga aatcggcaag gctaccgcca gtacttctt ctacagcaac   3240
atcatgaact tttcaagac cgagattacc ctggccaacg gcgagatccg gaagcggcct   3300
```

```
ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga acagcgataa gctgatcgcc    3480
agaaagaagg actgggaccc taagaagtac ggcggcttcg acagcccac cgtggcctat    3540
tctgtgctgg tggtggccaa agtggaaaag ggcaagtcca agaaactgaa gagtgtgaaa    3600
gagctgctgg ggatcaccat catggaaaga agcagcttcg agaagaatcc catcgacttt    3660
ctggaagcca agggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gcctccaaa tatgtgaact tcctgtacct ggccagccac    3840
tatgagaagc tgaagggctc ccccgaggat aatgagcaga acagctgtt tgtgaacag    3900
cacaagcact acctggacga gatcatcgag cagatcagcg agttctccaa gagagtgatc    3960
ctggccgacg ctaatctgga caaagtgctg tccgcctaca acaagcaccg ggataagccc    4020
atcagagagc aggccgagaa tatcatccac ctgtttaccc tgaccaatct gggagccct    4080
gccgccttca gtactttga caccaccatc gaccggaaga ggtacaccag caccaaagag    4140
gtgctggacg ccaccctgat ccaccagagc atcaccggcc tgtacgagac acggatcgac    4200
ctgtctcagc tgggaggcga cggtggctct ggaggcggat caggtatgaa gctactgtct    4260
tctatcgaac aagcatgcga tatttgccga cttaaaaagc tcaagtgctc caagaaaaa    4320
ccgaagtgcg ccaagtgtct gaagaacaac tgggagtgtc gctactctcc caaaaccaaa    4380
aggtctccgc tgactagggc acatctgaca gaagtggaat caaggctaga aagactggaa    4440
cagctatttc tactgatttt tcctcgagaa gaccttgaca tgattttgaa aatggattct    4500
ttacaggata taaaagcatt gttaacagga ttatttgtgc aagataatgt gaataaagat    4560
gccgtcacag atagattggc ttcagtggag actgatatgc ctctaacatt gagacagcat    4620
agaataagtg cgacatcatc atcggaagag agtagtaaca aaggtcaaag acagttgact    4680
gtatcgggtg gctctggagg cggatcaggt aaaaggccgg cggccacgaa aaaggccggc    4740
caggcaaaaa agaaaaag                                                 4758
```

<210> SEQ ID NO 15
<211> LENGTH: 1586
<212> TYPE: PRT
<213> ORGANISM: Artificial Sequence
<220> FEATURE:
<223> OTHER INFORMATION: Synthetic

<400> SEQUENCE: 15

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Asp Lys Lys Tyr Ser Ile Gly Leu
        35                  40                  45

Asp Ile Gly Thr Asn Ser Val Gly Trp Ala Val Ile Thr Asp Glu Tyr
    50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95
```

```
Thr Ala Glu Ala Thr Arg Leu Lys Arg Thr Ala Arg Arg Tyr Thr
                100                 105                 110
Arg Arg Lys Asn Arg Ile Cys Tyr Leu Gln Glu Ile Phe Ser Asn Glu
            115                 120                 125
Met Ala Lys Val Asp Asp Ser Phe Phe His Arg Leu Glu Glu Ser Phe
        130                 135                 140
Leu Val Glu Glu Asp Lys Lys His Glu Arg His Pro Ile Phe Gly Asn
145                 150                 155                 160
Ile Val Asp Glu Val Ala Tyr His Glu Lys Tyr Pro Thr Ile Tyr His
                165                 170                 175
Leu Arg Lys Lys Leu Val Asp Ser Thr Asp Lys Ala Asp Leu Arg Leu
            180                 185                 190
Ile Tyr Leu Ala Leu Ala His Met Ile Lys Phe Arg Gly His Phe Leu
        195                 200                 205
Ile Glu Gly Asp Leu Asn Pro Asp Asn Ser Asp Val Asp Lys Leu Phe
    210                 215                 220
Ile Gln Leu Val Gln Thr Tyr Asn Gln Leu Phe Glu Glu Asn Pro Ile
225                 230                 235                 240
Asn Ala Ser Gly Val Asp Ala Lys Ala Ile Leu Ser Ala Arg Leu Ser
                245                 250                 255
Lys Ser Arg Arg Leu Glu Asn Leu Ile Ala Gln Leu Pro Gly Glu Lys
            260                 265                 270
Lys Asn Gly Leu Phe Gly Asn Leu Ile Ala Leu Ser Leu Gly Leu Thr
        275                 280                 285
Pro Asn Phe Lys Ser Asn Phe Asp Leu Ala Glu Asp Ala Lys Leu Gln
    290                 295                 300
Leu Ser Lys Asp Thr Tyr Asp Asp Asp Leu Asp Asn Leu Leu Ala Gln
305                 310                 315                 320
Ile Gly Asp Gln Tyr Ala Asp Leu Phe Leu Ala Ala Lys Asn Leu Ser
                325                 330                 335
Asp Ala Ile Leu Leu Ser Asp Ile Leu Arg Val Asn Thr Glu Ile Thr
            340                 345                 350
Lys Ala Pro Leu Ser Ala Ser Met Ile Lys Arg Tyr Asp Glu His His
        355                 360                 365
Gln Asp Leu Thr Leu Leu Lys Ala Leu Val Arg Gln Gln Leu Pro Glu
    370                 375                 380
Lys Tyr Lys Glu Ile Phe Phe Asp Gln Ser Lys Asn Gly Tyr Ala Gly
385                 390                 395                 400
Tyr Ile Asp Gly Gly Ala Ser Gln Glu Glu Phe Tyr Lys Phe Ile Lys
                405                 410                 415
Pro Ile Leu Glu Lys Met Asp Gly Thr Glu Glu Leu Leu Val Lys Leu
            420                 425                 430
Asn Arg Glu Asp Leu Leu Arg Lys Gln Arg Thr Phe Asp Asn Gly Ser
        435                 440                 445
Ile Pro His Gln Ile His Leu Gly Glu Leu His Ala Ile Leu Arg Arg
    450                 455                 460
Gln Glu Asp Phe Tyr Pro Phe Leu Lys Asp Asn Arg Glu Lys Ile Glu
465                 470                 475                 480
Lys Ile Leu Thr Phe Arg Ile Pro Tyr Tyr Val Gly Pro Leu Ala Arg
                485                 490                 495
Gly Asn Ser Arg Phe Ala Trp Met Thr Arg Lys Ser Glu Glu Thr Ile
            500                 505                 510
Thr Pro Trp Asn Phe Glu Glu Val Val Asp Lys Gly Ala Ser Ala Gln
```

-continued

```
            515                 520                 525
Ser Phe Ile Glu Arg Met Thr Asn Phe Asp Lys Asn Leu Pro Asn Glu
    530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
            580                 585                 590

Lys Thr Asn Arg Lys Val Thr Val Lys Gln Leu Lys Glu Asp Tyr Phe
        595                 600                 605

Lys Lys Ile Glu Cys Phe Asp Ser Val Glu Ile Ser Gly Val Glu Asp
    610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
            660                 665                 670

Glu Arg Leu Lys Thr Tyr Ala His Leu Phe Asp Asp Lys Val Met Lys
        675                 680                 685

Gln Leu Lys Arg Arg Arg Tyr Thr Gly Trp Gly Arg Leu Ser Arg Lys
    690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
        755                 760                 765

Ser Pro Ala Ile Lys Lys Gly Ile Leu Gln Thr Val Lys Val Val Asp
    770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
            820                 825                 830

Gln Ile Leu Lys Glu His Pro Val Glu Asn Thr Gln Leu Gln Asn Glu
        835                 840                 845

Lys Leu Tyr Leu Tyr Tyr Leu Gln Asn Gly Arg Asp Met Tyr Val Asp
    850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
                885                 890                 895

Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
        915                 920                 925

Lys Leu Ile Thr Gln Arg Lys Phe Asp Asn Leu Thr Lys Ala Glu Arg
    930                 935                 940
```

```
Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                965                 970                 975

Arg Met Asn Thr Lys Tyr Asp Glu Asn Asp Lys Leu Ile Arg Glu Val
            980                 985                 990

Lys Val Ile Thr Leu Lys Ser Lys  Leu Val Ser Asp Phe  Arg Lys Asp
        995                 1000                1005

Phe Gln Phe Tyr Lys Val Arg  Glu Ile Asn Asn Tyr  His His Ala
    1010            1015                1020

His Asp Ala Tyr Leu Asn Ala  Val Val Gly Thr Ala  Leu Ile Lys
    1025            1030                1035

Lys Tyr Pro Lys Leu Glu Ser  Glu Phe Val Tyr Gly  Asp Tyr Lys
    1040            1045                1050

Val Tyr Asp Val Arg Lys Met  Ile Ala Lys Ser Glu  Gln Glu Ile
    1055            1060                1065

Gly Lys Ala Thr Ala Lys Tyr  Phe Phe Tyr Ser Asn  Ile Met Asn
    1070            1075                1080

Phe Phe Lys Thr Glu Ile Thr  Leu Ala Asn Gly Glu  Ile Arg Lys
    1085            1090                1095

Arg Pro Leu Ile Glu Thr Asn  Gly Glu Thr Gly Glu  Ile Val Trp
    1100            1105                1110

Asp Lys Gly Arg Asp Phe Ala  Thr Val Arg Lys Val  Leu Ser Met
    1115            1120                1125

Pro Gln Val Asn Ile Val Lys  Lys Thr Glu Val Gln  Thr Gly Gly
    1130            1135                1140

Phe Ser Lys Glu Ser Ile Leu  Pro Lys Arg Asn Ser  Asp Lys Leu
    1145            1150                1155

Ile Ala Arg Lys Lys Asp Trp  Asp Pro Lys Lys Tyr  Gly Gly Phe
    1160            1165                1170

Asp Ser Pro Thr Val Ala Tyr  Ser Val Leu Val Val  Ala Lys Val
    1175            1180                1185

Glu Lys Gly Lys Ser Lys Lys  Leu Lys Ser Val Lys  Glu Leu Leu
    1190            1195                1200

Gly Ile Thr Ile Met Glu Arg  Ser Ser Phe Glu Lys  Asn Pro Ile
    1205            1210                1215

Asp Phe Leu Glu Ala Lys Gly  Tyr Lys Glu Val Lys  Lys Asp Leu
    1220            1225                1230

Ile Ile Lys Leu Pro Lys Tyr  Ser Leu Phe Glu Leu  Glu Asn Gly
    1235            1240                1245

Arg Lys Arg Met Leu Ala Ser  Ala Gly Glu Leu Gln  Lys Gly Asn
    1250            1255                1260

Glu Leu Ala Leu Pro Ser Lys  Tyr Val Asn Phe Leu  Tyr Leu Ala
    1265            1270                1275

Ser His Tyr Glu Lys Leu Lys  Gly Ser Pro Glu Asp  Asn Glu Gln
    1280            1285                1290

Lys Gln Leu Phe Val Glu Gln  His Lys His Tyr Leu  Asp Glu Ile
    1295            1300                1305

Ile Glu Gln Ile Ser Glu Phe  Ser Lys Arg Val Ile  Leu Ala Asp
    1310            1315                1320

Ala Asn Leu Asp Lys Val Leu  Ser Ala Tyr Asn Lys  His Arg Asp
    1325            1330                1335
```

| | | | | | | | | | | | |
|---|---|---|---|---|---|---|---|---|---|---|---|
|Lys|Pro|Ile|Arg|Glu|Gln|Ala|Glu|Asn|Ile|Ile|His|Leu|Phe|Thr|
| |1340| | | |1345| | | |1350| | | | | |

Lys Pro Ile Arg Glu Gln Ala Glu Asn Ile Ile His Leu Phe Thr
    1340            1345            1350

Leu Thr Asn Leu Gly Ala Pro Ala Ala Phe Lys Tyr Phe Asp Thr
    1355            1360            1365

Thr Ile Asp Arg Lys Arg Tyr Thr Ser Thr Lys Glu Val Leu Asp
    1370            1375            1380

Ala Thr Leu Ile His Gln Ser Ile Thr Gly Leu Tyr Glu Thr Arg
    1385            1390            1395

Ile Asp Leu Ser Gln Leu Gly Gly Asp Gly Gly Ser Gly Gly Gly
    1400            1405            1410

Ser Gly Met Lys Leu Leu Ser Ser Ile Glu Gln Ala Cys Asp Ile
    1415            1420            1425

Cys Arg Leu Lys Lys Leu Lys Cys Ser Lys Glu Lys Pro Lys Cys
    1430            1435            1440

Ala Lys Cys Leu Lys Asn Asn Trp Glu Cys Arg Tyr Ser Pro Lys
    1445            1450            1455

Thr Lys Arg Ser Pro Leu Thr Arg Ala His Leu Thr Glu Val Glu
    1460            1465            1470

Ser Arg Leu Glu Arg Leu Glu Gln Leu Phe Leu Leu Ile Phe Pro
    1475            1480            1485

Arg Glu Asp Leu Asp Met Ile Leu Lys Met Asp Ser Leu Gln Asp
    1490            1495            1500

Ile Lys Ala Leu Leu Thr Gly Leu Phe Val Gln Asp Asn Val Asn
    1505            1510            1515

Lys Asp Ala Val Thr Asp Arg Leu Ala Ser Val Glu Thr Asp Met
    1520            1525            1530

Pro Leu Thr Leu Arg Gln His Arg Ile Ser Ala Thr Ser Ser Ser
    1535            1540            1545

Glu Glu Ser Ser Asn Lys Gly Gln Arg Gln Leu Thr Val Ser Gly
    1550            1555            1560

Gly Ser Gly Gly Gly Ser Gly Lys Arg Pro Ala Ala Thr Lys Lys
    1565            1570            1575

Ala Gly Gln Ala Lys Lys Lys Lys
    1580            1585

<210> SEQ ID NO 16
<211> LENGTH: 9175
<212> TYPE: DNA
<213> ORGANISM: Artificial Sequence
<220> FEATURE:
<223> OTHER INFORMATION: Synthetic

<400> SEQUENCE: 16

```
gagggcctat tcccatgat tccttcatat ttgcatatac gatacaaggc tgttagagag      60
ataattggaa ttaatttgac tgtaaacaca agatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacaccg gtcttcgag aagacctgtt ttagagctag aaatagcaag ttaaataag     300 gctagtccgt tatcaacttg aaaaagtggc accgagtcgg tgctttttg ttttagagct     360 agaaatagca agttaaaata aggctagtcc gtttttagcg cgtgcgccaa ttctgcagac     420
aaatggctct agaggtaccc gttacataac ttacggtaaa tggcccgcct ggctgaccgc     480
ccaacgaccc ccgcccattg acgtcaatag taacgccaat agggactttc cattgacgtc     540
```

```
aatgggtgga gtatttacgg taaactgccc acttggcagt acatcaagtg tatcatatgc    600
caagtacgcc ccctattgac gtcaatgacg gtaaatggcc cgcctggcat tgtgcccagt    660
acatgacctt atgggacttt cctacttggc agtacatcta cgtattagtc atcgctatta    720
ccatggtcga ggtgagcccc acgttctgct tcactctccc catctccccc ccctccccac    780
ccccaatttt gtatttattt attttttaat tattttgtgc agcgatgggg gcggggggg    840
ggggggggcg cgcgccaggc ggggcggggc ggggcgaggg gcgggcggg gcgaggcgga    900
gaggtgcggc ggcagccaat cagagcggcg cgctccgaaa gtttccttt atggcgaggc    960
ggcggcggcg gcgccctat aaaaagcgaa gcgcgcggcg gcgggagtc gctgcgacgc    1020
tgccttcgcc ccgtgccccg ctccgccgcc gcctcgcgcc gcccgcccg gctctgactg    1080
accgcgttac tcccacaggt gagcgggcgg gacggcccct tcctccgggg ctgtaattag    1140
ctgagcaaga ggtaagggtt taagggatgg ttggttggtg gggtattaat gtttaattac    1200
ctggagcacc tgcctgaaat cacttttttt caggttggac cggtgccacc atggactata    1260
aggaccacga cggagactac aaggatcatg atattgatta caaagacgat gacgataaga    1320
tggccccaaa gaagaagcgg aaggtcggta tccacggagt cccagcagcc gacaagaagt    1380
acagcatcgg cctggacatc ggcaccaact ctgtgggctg ggccgtgatc accgacgagt    1440
acaaggtgcc cagcaagaaa ttcaaggtgc tgggcaacac cgaccggcac agcatcaaga    1500
agaacctgat cggagccctg ctgttcgaca gcggcgaaac agccgaggcc acccggctga    1560
agagaaccgc cagaagaaga taccagac ggaagaaccg gatctgctat ctgcaagaga    1620
tcttcagcaa cgagatggcc aaggtggacg acagcttctt ccacagactg gaagagtcct    1680
tcctggtgga agaggataag aagcacgagc ggcacccccat cttcggcaac atcgtggacg    1740
aggtggccta ccacgagaag taccccacca tctaccacct gagaaagaaa ctggtggaca    1800
gcaccgacaa ggccgacctg cggctgatct atctggccct ggcccacatg atcaagttcc    1860
ggggccactt cctgatcgag ggcgacctga accccgacaa cagcgacgtg gacaagctgt    1920
tcatccagct ggtgcagacc tacaaccagc tgttcgagga aaaccccatc aacgccagcg    1980
gcgtggacgc caaggccatc ctgtctgcca gactgagcaa gagcagacgg ctggaaaatc    2040
tgatcgccca gctgcccggc gagaagaaga atggcctgtt cggaaacctg attgccctga    2100
gcctgggcct gaccccccaac ttcaagagca acttcgacct ggccgaggat gccaaactgc    2160
agctgagcaa ggacacctac gacgacgacc tggacaacct gctggcccag atcggcgacc    2220
agtacgccga cctgttttctg gccgccaaga acctgtccga cgccatcctg ctgagcgaca    2280
tcctgagagt gaacaccgag atcaccaagg ccccctgag cgcctctatg atcaagagat    2340
acgacgagca ccaccaggac ctgaccctgc tgaaagctct cgtgcggcag cagctgcctg    2400
agaagtacaa agagattttc ttcgaccaga gcaagaacgg ctacgccggc tacattgacg    2460
gcggagccag ccaggaagag ttctacaagt tcatcaagcc catcctggaa aagatggacg    2520
gcaccgagga actgctcgtg aagctgaaca gagaggacct gctgcggaag cagcggacct    2580
tcgacaacgg cagcatcccc caccagatcc acctgggaga gctgcacgcc attctgcggc    2640
ggcaggaaga tttttaccca ttcctgaagg acaaccggga aaagatcgag aagatcctga    2700
ccttccgcat cccctactac gtgggccctc tggccagggg aaacagcaga ttcgcctgga    2760
tgaccagaaa gagcgaggaa accatcaccc cctggaactt cgaggaagtg gtggacaagg    2820
gcgcttccgc ccagagcttc atcgagcgga tgaccaactt cgataagaac ctgcccaacg    2880
agaaggtgct gcccaagcac agcctgctgt acgagtactt caccgtgtat aacgagctga    2940
```

```
ccaaagtgaa atacgtgacc gagggaatga gaaagcccgc cttcctgagc ggcgagcaga    3000
aaaaggccat cgtggacctg ctgttcaaga ccaaccggaa agtgaccgtg aagcagctga    3060
aagaggacta cttcaagaaa atcgagtgct tcgactccgt ggaaatctcc ggcgtggaag    3120
atcggttcaa cgcctccctg gcacatacc acgatctgct gaaaattatc aaggacaagg     3180
acttcctgga caatgaggaa aacgaggaca ttctggaaga tatcgtgctg accctgacac    3240
tgtttgagga cagagagatg atcgaggaac ggctgaaaac ctatgcccac ctgttcgacg    3300
acaaagtgat gaagcagctg aagcggcgga gataccggg ctggggcagg ctgagccgga    3360
agctgatcaa cggcatccgg acaagcagt ccggcaagca aatcctggat ttcctgaagt     3420
ccgacggctt cgccaacaga aacttcatgc agctgatcca cgacgacagc ctgacccttta  3480 aagaggacat ccagaaagcc caggtgtccg gccagggcga tagcctgcac gagcacattg    3540
ccaatctggc cggcagcccc gccattaaga agggcatcct gcagacagtg aaggtggtgg    3600
acgagctcgt gaaagtgatg ggccggcaca agcccgagaa catcgtgatc gaaatggcca    3660
gagagaacca gaccacccag aagggacaga agaacagccg cgagagaatg aagcggatcg    3720
aagagggcat caaagagctg ggcagccaga tcctgaaaga acaccccgtg gaaaacaccc    3780
agctgcagaa cgagaagctg tacctgtact acctgcagaa tgggcgggat atgtacgtgg    3840
accaggaact ggacatcaac cggctgtccg actacgatgt ggaccatatc gtgcctcaga    3900
gctttctgaa ggacgactcc atcgacaaca aggtgctgac cagaagcgac aagaaccggg    3960
gcaagagcga caacgtgccc tccgaagagg tcgtgaagaa gatgaagaac tactggcggc    4020
agctgctgaa cgccaagctg attacccaga gaaagttcga caatctgacc aaggccgaga    4080
gaggcggcct gagcgaactg gataaggccg gcttcatcaa gagacagctg gtggaaaccc    4140
ggcagatcac aaagcacgtg gcacagatcc tggactcccg gatgaacact aagtacgacg    4200
agaatgacaa gctgatccgg gaagtgaaag tgatcaccct gaagtccaag ctggtgtccg    4260
atttccggaa ggatttccag ttttacaaag tgcgcgagat caacaactac caccacgccc    4320
acgacgccta cctgaacgcc gtcgtgggaa ccgccctgat caaaaagtac cctaagctgg    4380
aaagcgagtt cgtgtacggc gactacaagg tgtacgacgt gcggaagatg atcgccaaga    4440
gcgagcagga aatcggcaag gctaccgcca agtacttctt ctacagcaac atcatgaact    4500
ttttcaagac cgagattacc ctggccaacg gcgagatccg gaagcggcct ctgatcgaga    4560
caaacggcga aaccggggag atcgtgtggg ataagggccg ggattttgcc accgtgcgga    4620
aagtgctgag catgccccaa gtgaatatcg tgaaaaagac cgaggtgcag acaggcggct    4680
tcagcaaaga gtctatcctg cccaagagga acagcgataa gctgatcgcc agaaagaagg    4740
actgggaccc taagaagtac ggcggcttcg acagccccac cgtggcctat tctgtgctgg    4800
tggtggccaa agtggaaaag ggcaagtcca gaaaactgaa gagtgtgaaa gagctgctgg    4860
ggatcaccat catggaaaga agcagcttcg agaagaatcc catcgacttt ctggaagcca    4920
agggctacaa agaagtgaaa aaggacctga tcatcaagct gcctaagtac tccctgttcg    4980
agctggaaaa cggccggaag agaatgctgg cctctgccgg cgaactgcag aagggaaacg    5040 aactggcccct gccctccaaa tatgtgaact tcctgtacct ggccagccac tatgagaagc    5100
tgaagggctc ccccgaggat aatgagcaga aacagctgtt tgtggaacag cacaagcact    5160
acctggacga gatcatcgag cagatcagcg agttctccaa gagagtgatc ctggccgaca    5220
ctaatctgga caaagtgctg tccgcctaca acaagcaccg ggataagccc atcagagagc    5280
```

```
aggccgagaa tatcatccac ctgtttaccc tgaccaatct gggagcccct gccgccttca   5340
agtactttga caccaccatc gaccggaaga ggtacaccag caccaaagag gtgctggacg   5400
ccaccctgat ccaccagagc atcaccggcc tgtacgagac acggatcgac ctgtctcagc   5460
tgggaggcga caaaaggccg gcggccacga aaaaggccgg ccaggcaaaa agaaaaagg    5520 aattcggcag tggagagggc agaggaagtc tgctaacatg cggtgacgtc gaggagaatc   5580
ctggcccaat gaccgagtac aagcccacgg tgcgcctcgc cacccgcgac gacgtcccca   5640
gggccgtacg cacccttcgcc gccgcgttcg ccgactaccc cgccacgcgc cacaccgtcg   5700
atccggaccg ccacatcgag cgggtcaccg agctgcaaga actcttcctc acgcgcgtcg   5760
ggctcgacat cggcaaggtg tgggtcgcgg acgacggcgc cgcggtggcg gtctggacca   5820
cgccggagag cgtcgaagcg ggggcggtgt tcgccgagat cggcccgcgc atggccgagt   5880
tgagcggttc ccggctggcc gcgcagcaac agatggaagg cctcctggcg ccgcaccggc   5940
ccaaggagcc cgcgtggttc ctggccaccg tcggagtctc gcccgaccac cagggcaagg   6000
gtctgggcag cgccgtcgtg ctccccggag tggaggcggc cgagcgcgcc ggggtgcccg   6060
ccttcctgga gacctccgcg ccccgcaacc tccccttcta cgagcggctc ggcttcaccg   6120
tcaccgccga cgtcgaggtg cccgaaggac cgcgcacctg gtgcatgacc cgcaagcccg   6180
gtgcctgaga attctaacta gagctcgctg atcagcctcg actgtgcctt ctagttgcca   6240
gccatctgtt gtttgcccct cccccgtgcc ttccttgacc ctggaaggtg ccactcccac   6300
tgtcctttcc taataaaatg aggaaattgc atcgcattgt ctgagtaggt gtcattctat   6360
tctggggggt ggggtggggc aggacagcaa ggggaggat tggaagaga atagcaggca     6420 tgctggggag cggccgcagg aacccctagt gatggagttg ccactccct ctctgcgcgc    6480 tcgctcgctc actgaggccg ggcgaccaaa ggtcgcccga cgcccgggct ttgcccgggc   6540
ggcctcagtg agcgagcgag cgcgcagctg cctgcagggg cgcctgatgc ggtattttct   6600
ccttacgcat ctgtgcggta tttcacaccg catacgtcaa agcaaccata gtacgcgccc   6660
tgtagcggcg cattaagcgc ggcgggtgtg gtggttacgc gcagcgtgac cgctacactt   6720
gccagcgccc tagcgcccgc tcctttcgct ttcttccctt cctttctcgc cacgttcgcc   6780
ggctttcccc gtcaagctct aaatcggggg ctccctttag ggttccgatt tagtgcttta   6840
cggcacctcg accccaaaaa acttgatttg ggtgatggtt cacgtagtgg gccatcgccc   6900
tgatagacgg ttttttcgccc tttgacgttg gagtccacgt tctttaatag tggactcttg   6960
ttccaaactg gaacaacact caaccctatc tcgggctatt cttttgattt ataagggatt    7020
ttgccgattt cggcctattg gttaaaaaat gagctgattt aacaaaaatt taacgcgaat   7080
tttaacaaaa tattaacgtt tacaattta tggtgcactc tcagtacaat ctgctctgat    7140
gccgcatagt taagccagcc ccgacacccg ccaacacccg ctgacgcgcc ctgacgggct   7200
tgtctgctcc cggcatccgc ttacagacaa gctgtgaccg tctccgggag ctgcatgtgt    7260
cagaggtttt caccgtcatc accgaaacgc gcgagacgaa agggcctcgt gatacgccta   7320
tttttatagg ttaatgtcat gataataatg gtttcttaga cgtcaggtgg cacttttcgg   7380
ggaaatgtgc gcggaacccc tatttgttta ttttctaaa tacattcaaa tatgtatccg   7440
ctcatgagac aataaccctg ataaatgctt caataatatt gaaaaggaa gagtatgagt   7500 attcaacatt tccgtgtcgc ccttattccc ttttttgcgg cattttgcct tcctgttttt   7560
gctcacccag aaacgctggt gaaagtaaaa gatgctgaag atcagttggg tgcacgagtg   7620
ggttacatcg aactggatct caacagcggt aagatccttg agagttttcg ccccgaagaa   7680
```

-continued

```
cgttttccaa tgatgagcac ttttaaagtt ctgctatgtg gcgcggtatt atcccgtatt    7740
gacgccgggc aagagcaact cggtcgccgc atacactatt ctcagaatga cttggttgag    7800
tactcaccag tcacagaaaa gcatcttacg gatggcatga cagtaagaga attatgcagt    7860
gctgccataa ccatgagtga taacactgcg gccaacttac ttctgacaac gatcggagga    7920
ccgaaggagc taaccgcttt tttgcacaac atggggatc atgtaactcg ccttgatcgt    7980
tgggaaccgg agctgaatga agccatacca aacgacgagc gtgacaccac gatgcctgta    8040
gcaatggcaa caacgttgcg caaactatta actggcgaac tacttactct agcttcccgg    8100
caacaattaa tagactggat ggaggcggat aaagttgcag gaccacttct gcgctcggcc    8160
cttccggctg gctggtttat tgctgataaa tctggagccg gtgagcgtgg aagccgcggt    8220
atcattgcag cactggggcc agatggtaag ccctcccgta tcgtagttat ctacacgacg    8280
gggagtcagg caactatgga tgaacgaaat agacagatcg ctgagatagg tgcctcactg    8340
attaagcatt ggtaactgtc agaccaagtt tactcatata tactttagat tgatttaaaa    8400
cttcattttt aatttaaaag gatctaggtg aagatccttt ttgataatct catgaccaaa    8460
atcccttaac gtgagttttc gttccactga gcgtcagacc ccgtagaaaa gatcaaagga    8520
tcttcttgag atcctttttt tctgcgcgta atctgctgct tgcaaacaaa aaaaccaccg    8580
ctaccagcgg tggtttgttt gccggatcaa gagctaccaa ctcttttcc gaaggtaact    8640 ggcttcagca gagcgcagat accaaatact gtccttctag tgtagccgta gttaggccac    8700
cacttcaaga actctgtagc accgcctaca tacctcgctc tgctaatcct gttaccagtg    8760
gctgctgcca gtggcgataa gtcgtgtctt accgggttgg actcaagacg atagttaccg    8820
gataaggcgc agcggtcggg ctgaacgggg ggttcgtgca cacagcccag cttggagcga    8880
acgacctaca ccgaactgag atacctacag cgtgagctat gagaaagcgc cacgcttccc    8940
gaagggagaa aggcggacag gtatccggta agcggcaggg tcggaacagg agagcgcacg    9000
agggagcttc caggggggaaa cgcctggtat ctttatagtc ctgtcgggtt tcgccacctc    9060
tgacttgagc gtcgattttt gtgatgctcg tcagggggc ggagcctatg gaaaaacgcc    9120
agcaacgcgg cctttttacg gttcctggcc ttttgctggc cttttgctca catgt         9175
```

<210> SEQ ID NO 17
<211> LENGTH: 24
<212> TYPE: DNA
<213> ORGANISM: Artificial Sequence
<220> FEATURE:
<223> OTHER INFORMATION: Synthetic

<400> SEQUENCE: 17
taacgcttgc tttcactgtt gtcc                                              24

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
atctcgtcat cgcctccatg t                                                 21

<210> SEQ ID NO 19
<211> LENGTH: 27
<212> TYPE: DNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: n may be a, g, t, or c.
<220> FEATURE:
<221> NAME/KEY: misc_feature
<222> LOCATION: (9)..(20)
<223> OTHER INFORMATION: n is a, g, t, or c.
<220> FEATURE:
<221> NAME/KEY: misc_feature
<222> LOCATION: (21)..(22)
<223> OTHER INFORMATION: n can be any nucleotide.
<220> FEATURE:
<221> NAME/KEY: misc_feature
<222> LOCATION: (27)..(27)
<223> OTHER INFORMATION: w is a or t.

<400> SEQUENCE: 19
nnnnnnnnnn nnnnnnnnnn nnagaaw                                      27

<210> SEQ ID NO 20
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(12)
<223> OTHER INFORMATION: n is a, g, t, or c.
<220> FEATURE:
<221> NAME/KEY: misc_feature
<222> LOCATION: (13)..(14)
<223> OTHER INFORMATION: n can be any nucleotide.
<220> FEATURE:
<221> NAME/KEY: misc_feature
<222> LOCATION: (19)..(19)
<223> OTHER INFORMATION: w is a or t.

<400> SEQUENCE: 20
nnnnnnnnnn nnnnagaaw                                               19
```

NUCLEASE WITH ENHANCED EFFICIENCY OF GENOME EDITING

CROSS-REFERENCE TO RELATED APPLICATIONS

This application is the national phase of International Application No. PCT/US2016/047937, filed Aug. 22, 2016, which claims priority to U.S. provisional patent application No. 62/207,860, filed Aug. 20, 2015, the disclosure of which is incorporated herein by reference.

FIELD OF THE INVENTION

The present invention generally relates to site-specific nuclease and gene editing.

REFERENCE TO SEQUENCE LISTING

This application contains the sequences shown in table below. A computer readable copy of the Sequence Listing is submitted along with this application, which is entitled "044903-8007US02-20191024_ST25" created on Oct. 24, 2019 and is 61 Kb in size. The computer readable copy of the sequence listing is incorporated herein by reference.

| SEQ ID NO | Annotation |
| --- | --- |
| 1 | peptide sequence of Cas9 protein |
| 2 | nucleotide sequence of Cas 9 gene |
| 3 | peptide Sequence of TALE domain |
| 4 | peptide Sequence of TALE domain |
| 5 | peptide sequence of zinc finger domain |
| 6 | peptide sequence of helix turn helix domain |
| 7 | peptide sequence of GAL4 protein |
| 8 | nucleotide sequence of GAL4 gene |
| 9 | nucleotide sequence of 5 × UAS |
| 10 | nucleotide sequence of gRNA for targeting ROSA26 |
| 11 | nucleotide sequence of 60 bp insertion used in EXAMPLE 1 |
| 12 | nucleotide sequence of 5' Homologous arm used in EXAMPLE 1 |
| 13 | nucleotide sequence of 3' Homologous arm used in EXAMPLE 1 |
| 14 | nucleotide sequence of Cas9-GAL4 gene |
| 15 | peptide sequence of CAS9-GAL4 protein |
| 16 | nucleotide sequence of pX459 plasmid |
| 17 | nucleotide sequence of ROSA 5' primer |
| 18 | nucleotide sequence of ROSA insert 3' primer |

BACKGROUND OF THE INVENTION

RNA-guided Cas9 nucleases derived from clustered regularly interspaced short palindromic repeats (CRISPR)-Cas systems have provided a versatile tool for editing the genome of diverse organisms. However, current technologies based on CRISPR-Cas system have limited ability of inserting DNA fragments, e.g., gene knock-in. Therefore, there remains a need for new genome engineering technologies that are affordable, easy to set up and provide enhanced efficiency of gene knock-in.

BRIEF SUMMARY OF THE INVENTION

Figure 1:
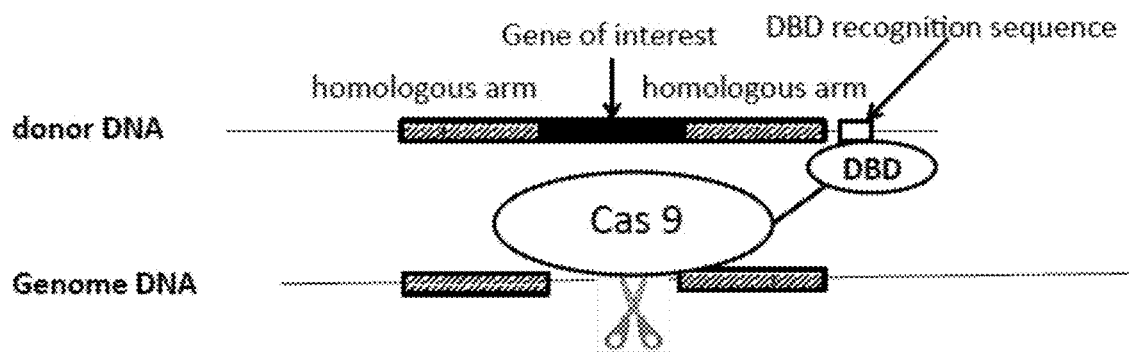
FIG. 1 is a schematic illustration of recombination mediated by a sequence-specific nuclease composition. The composition includes a Cas9-DBD (DNA binding domain) fusion protein and a donor vector containing a DBD recognition sequence. The Cas9 domain, in the guidance of a gRNA, cleaves the target site, while the DBD brings the donor vector to the vicinity of the target site. The gene of interest then inserts to the target site through recombination with increased efficiency.

Disclosed herein are compositions having site-specific nuclease activity with improved efficiency of inserting a nucleotide sequence into a target DNA. Also disclosed are methods of using the compositions.

In one aspect, the present disclosure provides a composition comprising a site-specific nuclease domain capable of cleaving a target DNA sequence; and a sequence-specific DNA binding domain capable of specifically binding to a recognition DNA sequence, wherein the site-specific nuclease domain operably links to the sequence-specific DNA binding domain.

In one embodiment, the site-specific nuclease domain is a CRISPR-associated (Cas) nuclease. In one embodiment, the Cas nuclease is Cas9.

In one embodiment, the composition further comprises a CRISPR-Cas guide RNA directed to the first nucleotide sequence.

In one embodiment, the site-specific nuclease domain is a transcription activator-like effector nuclease (TALEN).

In one embodiment, the site-specific nuclease domain is a zinc finger nuclease (ZFN).

In one embodiment, the sequence-specific DNA binding domain is selected from the group consisting of a transcription activator-like effector (TALE) domain, a zinc finger domain, an RNA-guided DNA-binding domain, a helix-turn-helix domain, a helix-loop-helix domain, a leucine zipper domain, a winged helix domain, an HMG-box domain, a Wor3 domain, a winged helix turn helix domain, and a B3 domain.

In one embodiment, the composition further comprises a donor vector comprising the recognition DNA sequence and a replacement DNA sequence.

In another aspect, the present disclosure provides a composition comprising a first vector comprising a first polynucleotide encoding (1) a fusion protein comprising a site-specific nuclease domain capable of cleaving a target DNA sequence; and (2) a sequence-specific DNA binding domain capable of specifically binding to a recognition DNA sequence.

In certain embodiments, the site-specific nuclease domain is a Cas nuclease. In one embodiment, the Cas nuclease is Cas9.

In one embodiments, the composition further comprises a second vector comprising a second polynucleotide encoding a CRISPR-Cas guide RNA directed to the target DNA sequence, wherein the first vector and the second vector is the same or different.

In one embodiment, the site-specific nuclease domain is a TALEN.

In one embodiment, the site-specific nuclease domain is a ZFN.

In the sequence-specific DNA binding domain is selected from the group consisting of a TALE domain, a zinc finger domain, an RNA-guided DNA-binding domain, a helix-turn-helix domain, a helix-loop-helix domain, a leucine zipper domain, a winged helix domain, an HMG-box domain, a Wor3 domain, a winged helix turn helix domain, and a B3 domain.

In one embodiment, the composition further comprises a donor vector comprising the recognition DNA sequence and a replacement DNA sequence.

In another aspect, the present disclosure provides a cell comprising the composition as described herein.

In another aspect, the present disclosure provides a method for inserting a replacement DNA sequence into a target DNA sequence of a cell comprising introducing into the cell the composition as described herein.

DESCRIPTION OF THE INVENTION

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without there specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

Definitions

The meaning of certain terms and phrases employed in the specification, examples, and appended claims are provided. The definitions are not meant to be limiting in nature and serve to provide a clearer understanding of certain aspects of the present invention.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

The term "cell," when used in connection with expressing a sequence includes any cell that is suitable for expressing a recombinant nucleic acid sequence. Cells include those of prokaryotes and eukaryotes (single-cell or multiple-cell), bacterial cells (e.g., strains of E. coli, Bacillus spp., Streptomyces spp., etc.), mycobacteria cells, fungal cells, yeast cells (e.g., S. cerevisiae, S. pombe, P. pastoris, P. methanolica, etc.), plant cells, insect cells (e.g., SF-9, SF-21, baculovirus-infected insect cells, Trichoplusia ni, etc.), non-human animal cells, human cells, B cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, VVI38, MRC 5, Colo205, HB 8065, HL-60, (e.g., BHK21), Jurkat, Daudi, A431 (epidermal), CV-1, U937, 3T3, L cell, C127 cell, SP2/0, NS-O, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell).

The term "domain", according to its ordinary usage in the art, refers to a discrete continuous part of the amino acid sequence of a polypeptide that can be equated with a particular function.

The term "introduced" in the context of inserting a nucleic acid sequence into a cell, means "transfection", or 'transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The term "nucleic acid" encompasses DNA, RNA, single stranded or double stranded and chemical modification thereof. The terms "nucleic acid" and "polynucleotide" are used interchangeably herein.

The term "operably linked" refers to an arrangement of elements wherein the components so described are configured so as to perform their usual function. As used herein, two polypeptide domains can be operably linked through covalent (e.g., peptide bond) or non-covalent bond, directly or indirectly. A given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier. Vectors include, but are not necessarily limited to, expression vectors.

As used herein, the term "expression vector" refers to a plasmid, virus, phagemid, or other vehicle known in the art that has been manipulated by insertion or incorporation of heterologous DNA, such as nucleic acid encoding the fusion proteins herein or expression cassettes provided herein. Such expression vectors typically contain a promoter sequence for efficient transcription of the inserted nucleic acid in a cell. The expression vector typically contains an origin of replication, a promoter, as well as specific genes that permit phenotypic selection of transformed cells.

Composition of Site-Specific Nuclease

In one aspect, the present disclosure provides compositions having site-specific nuclease activity with improved efficiency of inserting a nucleotide sequence (e.g., a replacement DNA sequence) to a target DNA. In one embodiment, the composition contains a site-specific nuclease domain capable of cleaving a target DNA sequence and a sequence-specific DNA binding domain capable of specifically binding to a specific DNA sequence (a recognition sequence) in a donor construct, wherein the site-specific nuclease domain operably links to the sequence-specific DNA binding domain. The composition can mediate high efficiency of gene editing if introduced into a cell having the target DNA sequence, along with a donor construct containing the specific DNA sequence for DNA binding and a replacement DNA sequence. After being introduced into the cell, the composition cuts the target DNA via the site-specific nuclease domain and invokes the homologous recombination machinery to repair the DNA break. The sequence-specific DNA binding domain of the composition binds to the donor vector through the specific DNA sequence and pulls the replacement DNA sequence into the vicinity of the target DNA sequence, which facilitate the homologous recombination machinery to use the donor construct as a template to repair the DNA break at the target DNA sequence, resulting in the high efficiency of inserting the replacement DNA sequence to the target DNA.

Site-Specific Nuclease Domain

As used herein, a "nuclease" is an enzyme capable of cleaving the phosphodiester bonds between the nucleotide subunits of nucleic acids. A "nuclease domain" is an independently folded protein domain having nuclease activity. A "site-specific nuclease" refers to a nuclease whose functioning depends on a specific nucleotide sequence. Typically, a site-specific nuclease recognizes and binds to a specific nucleotide sequence and cuts a phosphodiester bond within the nucleotide sequence. Examples of site-specific nucleases include, without limitation, zinc finger nucleases (ZFNs), transcriptional activator-like effector nucleases (TALENs) and CRISPR (clustered regularly interspaced short palindromic repeats)-associated (Cas) nucleases.

A site-specific nuclease typically contains a DNA-binding domain and a DNA-cleavage domain. For example, a ZFN contains a DNA binding domain that typically contains between three and six individual zinc finger repeats and a nuclease domain that consists of the FokI restriction enzyme that is responsible for the cleavage of DNA. The DNA binding domain of ZFN can recognize between 9 and 18 base pairs. In the example of a TALEN, which contains a TALE domain and a DNA cleavage domain, the TALE domain contains a repeated highly conserved 33-34 amino acid sequence with the exception of the $12^{th}$ and $13^{th}$ amino acids, whose variation shows a strong correlation with specific nucleotide recognition. For another example, Cas9, a typical Cas nuclease, is composed of an N-terminal recognition domain and two endonuclease domains (RuvC domain and HNH domain) at the C-terminus.

In certain embodiments, the site-specific nuclease is a Cas protein. In such case, the composition may also contain a CRISPR-Cas guide RNA directed to the target DNA sequence to form a CRISPR complex at the target DNA sequence. A CRISPR complex is formed in junction with a Cas protein, a guide RNA, a target sequence with PAM at the 3' end, and a tracr RNA (which can be a fused with the guide RNA or separated from the guide RNA).

As used herein, a "Cas protein" refers to a polypeptide that binds to the guide RNA and exhibit nuclease activity. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2. Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of S. pyogenes Cas9 protein may be found in the SwissProt database under accession number Q99ZW2. In one example, Cas9 protein has the sequence of SEQ ID NO: 1. In some embodiments, the unmodified Cas protein has DNA cleavage activity. In some embodiments, the Cas protein directs cleavage of one or both strands at the location of a target sequence, such as within the target sequence and/or within the complement of the target sequence. In some embodiments, the Cas protein directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, the Cas protein is mutated such that the mutated Cas protein lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A.

As used herein, a "CRISPR-Cas guide RNA" or "guide RNA" refers to an RNA that directs sequence-specific binding of a CRISPR complex to the target sequence. Typically, a guide RNA comprises (i) a guide sequence that has sufficient complementarity with a target polynucleotide sequence to hybridize with the target sequence and (ii) a trans-activating cr (tracr) mate sequence. A guide RNA may further comprises a tracr RNA fused at the 3' end, resulting a single chimeric guide RNA. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106(1): 23-24; and PA Carr and GM Church, 2009, *Nature Biotechnology* 27(12): 1151-62).

As used herein, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher.

In some embodiments, the guide RNA comprises a guide sequence fused to a tracr sequence, i.e., the tracr sequence and tracr mate sequence are contained within a single transcript, such that hybridization between the two produces a transcript having a secondary structure, such as a hairpin. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. Preferred loop-forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In an embodiment of the present application, the guide RNA has at least two or more hairpins. In preferred embodiments, the guide RNA has two, three, four or five hairpins. In a further embodiment of the invention, the guide RNA has at most five hairpins. In some embodiments, the guide RNA further includes a transcription termination sequence, preferably a polyT sequence, for example six T nucleotides. In some embodiments, the tracr sequence is a separate transcript from a transcript comprising the tracr mate sequence. In certain embodiments, tracr sequence is in a separate vector from the guide RNA (see, e.g., US PG Pub No. 20140068797).

As used herein, the term Protospacer adjacent motif (PAM) refers to a DNA sequence immediately following the DNA sequence targeted by Cas protein. In some embodiments, PAM sequence is located at the 3' end of the target sequence and is required for the Cas protein to successfully bind to the target sequence. The PAM sequence varies by the species of the bacteria from which the Cas protein is derived. For example, the PAM sequence for Cas9 from *Steptococcus pyogenes* is NGG (N could be any of A, T, C or G). For another example, the PAM sequence for *Neisseria meningitides* is NNNNGATT. The PAM sequence for *Streptococcus thermophilus* is NNAGGAA. The PAM sequence for *Treponema denticola* is NAAAAC.

In certain embodiments, the sequence-specific nuclease domain is a zinc finger nuclease (ZFN). Zinc finger nucleases are artificial restriction enzymes generated by fusing a zinc finger DNA-binding domain to a DNA-cleavage domain. Zinc finger domain can be engineered to target specific desired DNA sequences, which directs the zinc finger nucleases to cleave the target DNA sequences.

Typically, a zinc finger DNA-binding domain contains three to six individual zinc finger repeats and can recognize between 9 and 18 base pairs. Each zinc finger repeat typically includes approximately 30 amino acids and comprises a ββα-fold stabilized by a zinc ion. Adjacent zinc finger repeats arranged in tandem are joined together by linker sequences.

Various strategies have been developed to engineer zinc finger domains to bind desired sequences, including both "modular assembly" and selection strategies that employ either phage display or cellular selection systems (Pabo C O et al., "Design and Selection of Novel Cys2His2 Zinc Finger Proteins" Annu. Rev. Biochem. (2001) 70: 313-40). The most straightforward method to generate new zinc-finger DNA-binding domains is to combine smaller zinc-finger repeats of known specificity. The most common modular assembly process involves combining three separate zinc finger repeats that can each recognize a 3 base pair DNA sequence to generate a 3-finger array that can recognize a 9 base pair target site. Other procedures can utilize either 1-finger or 2-finger modules to generate zinc-finger arrays with six or more individual zinc finger repeats. Alternatively, selection methods have been used to generate zinc-finger DNA-binding domains capable of targeting desired sequences. Initial selection efforts utilized phage display to select proteins that bound a given DNA target from a large pool of partially randomized zinc-finger domains. More recent efforts have utilized yeast one-hybrid systems, bacterial one-hybrid and two-hybrid systems, and mammalian cells. A promising new method to select novel zinc-finger arrays utilizes a bacterial two-hybrid system that combines pre-selected pools of individual zinc finger repeats that were each selected to bind a given triplet and then utilizes a second round of selection to obtain 3-finger repeats capable of binding a desired 9-bp sequence (Maeder M L, et al., "Rapid 'open-source' engineering of customized zinc-finger nucleases for highly efficient gene modification". Mol. Cell. (2008) 31 (2): 294-301).

The non-specific cleavage domain from the type II restriction endonuclease FokI is typically used as the cleavage domain in ZFNs. This cleavage domain must dimerize in order to cleave DNA and thus a pair of ZFNs are required to target non-palindromic DNA sites. Standard ZFNs fuse the cleavage domain to the C-terminus of each zinc finger domain. In order to allow the two cleavage domains to dimerize and cleave DNA, the two individual ZFNs must bind opposite strands of DNA with their C-termini a certain distance apart. The most commonly used linker sequences between the zinc finger domain and the cleavage domain requires the 5' edge of each binding site to be separated by 5 to 7 bp.

In certain embodiments, the sequence-specific nuclease domain is a transcription activator-like effector nuclease (TALEN). TALEN are artificial restriction enzymes made by fusing a transcription activator-like effector (TALE) DNA-binding domain to a DNA cleavage domain (e.g., a nuclease domain), which can be engineered to cut specific sequences. TALEs are proteins that are secreted by *Xanthomonas* bacteria via their type III secretion system when they infect plants. TALE DNA-binding domain contains a repeated highly conserved 33-34 amino acid sequence with divergent 12th and 13th amino acids, which are highly variable and show a strong correlation with specific nucleotide recognition. The relationship between amino acid sequence and DNA recognition allows for the engineering of specific DNA-binding domains by selecting a combination of repeat segments containing the appropriate variable amino acids. The non-specific DNA cleavage domain from the end of the FokI endonuclease can be used to construct TALEN. The FokI domain functions as a dimer, requiring two constructs with unique DNA binding domains for sites in the target gemone with proper orientation and spacing. See Boch, Jens "TALEs of genome targeting". Nature Biotechnology. (2011) 29 (2): 135-6; Boch, Jens et al., "Breaking the Code of DNA Binding Specificity of TAL-Type III Effectors" Science (2009) 326 (5959): 1509-12; Moscou M J and Bogdanove A J "A Simple Cipher Governs DNA Recognition by TAL Effectors" Science (2009) 326 (5959): 1501; Juillerat A et al., "Optimized tuning of TALEN specificity using non-conventional RVDs" Scientific Reports (2015) 5: 8150; Christian et al., "Targeting DNA Double-Strand Breaks with TAL Effector Nucleases" Genetics (2010) 186 (2): 757-61; Li et al., "TAL nucleases (TALNs): hybrid proteins composed of TAL effectors and FokI DNA-cleavage domain" Nucleic Acids Research (2010) 39: 1-14.

As used herein, a "target DNA sequence" refers to a sequence recognized by the site-specific nuclease domain. In some embodiments, the target DNA sequence is a sequence within a genome of a cell. Exemplary target sequences include those that are unique in the target genome. In some embodiments, a target DNA sequence is located in the nucleus or cytoplasm of a cell. In some embodiments, the target sequence may be within an organelle of a eukaryotic cell, for example, mitochondrion or chloroplast.

In certain embodiments that the site-specific nuclease domain is a Cas protein, a target sequence refers to a sequence to which a guide sequence is designed to have complementarity, where hybridization between a target sequence and a guide sequence promotes the formation of a CRISPR complex. The components of a CRISPR complex and the mechanism of using a CRISPR complex for gene editing has been described (e. g., M Jinek et al., Science, 2012, 337: 816-821; L Cong et al., Science, 2012, 339:819-823; PCT Publication WO2013176772, WO2013169802, WO2014018423 and U.S. Pat. No. 8,697,359). A target sequence can be any sequence in the genome of a target cell so long as the target sequence comprises a Protospacer Adjacent Motif (PAM) sequence, which is required by the formation of a CRISPR complex at the target sequence, at the 3' end of the target sequence. Exemplary target sequences include those that are unique in the genome of a target cell. For example, for the *S. pyogenes* Cas9, a unique target sequence in a genome may include a Cas9 target site of the form MMMMMMMMNNNNNNNNNNNNXGG where NNNNNNNNNNNNXGG (N is A, G, T, or C; and X can be any nucleotide) has a single occurrence in the genome. In this case, NNNNNNNNNNNN is complementary to a guid RNA and XGG is a PAM sequence. For the *S. therinophilus* CRISPR1Cas9, a unique target sequence in a genome may include a Cas9 target site of the form MMMMMMMMNNNNNNNNNNNNXXAGAAW (SEQ ID NO:19) where NNNNNNNNNNNNXXAGAAW (SEQ ID NO:20, N is A, G, T, or C; X can be any nucleotide; and W is A or T) has a single occurrence in the genome. In each of these sequences "M" may be A, G, T, or C, and need not be considered in identifying a sequence as unique.

Sequence-Specific DNA Binding Domain

In certain embodiments, the site-specific nuclease domain is operably linked to a sequence-specific DNA binding domain (DBD). A sequence-specific DNA binding domain is an independently folded protein domain that recognizes a specific DNA sequence. Examples of sequence-specific DNA binding domains include, without limitation, transcription activator-like effector domains, zinc finger domains, RNA-guided DNA-binding domain (e.g., Cas9 DNA binding domain), helix-turn-helix domains, helix-loop-helix domains, leucine zipper domains, winged helix domains, HMG-box domains, Wor3 domains, winged helix turn helix domains, and B3 domains.

The term "transcription activator-like effector domains" or "TALEs" or "TAL effectors" used herein is exchangeable and refers to a group of bacterial plant pathogen proteins that have been engineered into DNA binding domains with specificities, or an artificial version thereof. The TALE DNA binding domain can be multiple TALE repeats and each recognizes one DNA base pair via the above mentioned repeat variable di-residues (for example, the two amino acids of HD for recognition of C/G; NI for recognition of NT; NG for recognition of T/A; NS for recognition of C/G or NT or T/A or G/C; NN for recognition of G/C or A/T; IG for recognition of T/A; N for recognition of C/G; HG for recognition of C/G or T/A; H for recognition of T/A; and NK for recognition of G/C). The TALEs are usually fused to, such as transcription activator, repressor, or transcription activator-like effector nuclease domains (TALENs) to regulate or modify any desired gene due to its high specificity of the repeats and absence of context-dependent effects among repeats (Valton J et al., J Biol Chem. 2012 Nov. 9; 287(46): 38427-32). Thus, TALEs is considered a useful tool in gene editing, functional analysis, modification of gene expression and mutagenesis.

Exemplary TALE sequence of a repeat 34 amino acids can be LTPEQVVAIASNGGGKQALETVQRLLPVLCQAHG (SEQ ID NO: 3), or a repeat 35 amino acids can be LTPEQVVAIASNGGGKQALETVQRLLPVLCQAPHD (SEQ ID NO: 4) (for detailed description, please see U.S. Pat. No. 9,404,099). In certain embodiments, the TALE domains includes at least one repeat sequence having at least 40%, about 50%, about 60% or about 70% or about 80% or about 90% or about 95% or about 98%, or about 99% homology to a TALE.

"Zinc finger domains" are small, functional, independent folded domains stabilized by the coordination of one or more zinc ions via cysteine and/or histidine residues, which is a common eukaryotic DNA-binding protein. A Zinc finger domain structure contains multiple finger-like protrusions and tandemly contact target molecules. Due to its variety protein structures, Zinc finger domains can be classified into several different families and have different binding specificities. Different Zinc finger domains can interact with DNA, RNA, proteins and other small molecules. Engineered zinc finger can be fused to a DNA cleavage domain (e.g. Fok I cleavage domain) to generate a zinc finger nuclease (ZFN) for manipulating genomes. An exemplary zinc finger domain with conserved cysteine and histidine residues can be represented by -Cys-$(X)_{2-4}$-Cys-$(X)_{12}$-His-$(X)_{3-5}$-His- (SEQ ID NO: 5), wherein X can be any amino acid. For detailed description, please see U.S. Pat. No. 9,404,099. In certain embodiments, the DNA binding domain comprises one, two, three, or more zinc finger domains. In certain embodiments, the zinc finger domains bind the major groove of DNA.

"RNA-guided DNA-binding domain" refers to a DNA binding domain forms a complex with a guide RNA that guides the complex to a double stranded DNA, wherein the complex binds to the DNA sequence. In certain embodiments, the RNA-guided DNA binding domain is a Clustered Regularly Interspaced Short Palindromic Repeats associated (Cas) protein. In certain embodiments, the Cas protein is Cas9 DNA binding domain. In certain embodiments, the Cas9 DNA binding domain includes homologs and orthologs of Cas9 that can be guided by the RNA and retain the ability of DNA binding and cutting. In certain embodiments, the RNA-guided DNA-binding domain has a sequence that is at least 30%, 40%, 50%, 60%, 70%, 80%, 90%, 95%, 98% or 99% homologous to the Cas9 protein sequence from publicly available database, such as NCBI (e.g. GenBank Accession No.: AKS40389.1). In certain embodiments, the guide RNA can be CRISPR RNA (crRNA), trans-activating crRNA (trancrRNA) or crRNA-trancrRNA chimeric.

The helix-turn-helix domains or HTH domain is a structural motif of typically approximately 20 amino acids long that is capable of binding DNA that consists of two α helices separated by a short turn (Ann Rev. of Biochem. 1984. 53:293). The two α helices occupy the N- and C-terminus of the motif, respectively, and each fits into two successive major grooves. In certain embodiments, the HTH protein comprising one, two, three or more HTH domains. In eukaryotes, the HTH domain comprises three helices. An exemplary amino acid sequence of a HTH domain is Xaa1Xaa2Xaa3Xaa4AlaXaa6Xaa7Xaa8Gl yXaa10Xaa11Xaa12Xaa13Xaa14Xaa15Xaa16Xaa17 Xaa18Xaa19Xaa20 (SEQ ID NO: 6), where Xaa1, Xaa2, Xaa3, Xaa5, Xaa6, Xaa7, Xaa9, Xaa11, Xaa12, Xaa13, Xaa14, Xaa16, Xaa17, Xaa19, or Xaa20 is any amino acid and Xaa4, Xaa8, Xaa10, Xaa15, or Xaa18 is a hydrophobic amino acid (for detail, please see US patent application No. 2011/0230523).

The helix-loop-helix domain or HLH domain is an amino acid structural motif of a family of transcription factors having a conserved domain of 40-50 amino acid residues. HLH domain is a variation of the leucine zipper domain. The helix-loop-helix domain consists of two α helices connected by a loop. Transcription factors having such structures are dimeric via amphipathic helices. One helix of HLH domain is typically smaller than the other and, due to the flexibility of the loop, allows dimerization by folding and packing against another helix. The larger of the two helices typically contains the DNA binding region(s). Most HLH proteins have an extra basic region of about 15 amino acid residues adjacent to the HLH domain and specifically binds to DNA, and such HLH are referred as basic HLH (bHLH). Sequences of the bHLH domain can be obtained from public database, such as NCBI.

The leucine zipper domains (bZIP) is a three-dimensional structural motif consist of about 60-80 amino acids with a highly conserved DNA binding region of two specific a helices monomers (N-terminal) and a leucine zipper dimerization region of an amphipathic a helix (C-terminal). The basic residues of lysines and argnines in the N-terminal binds to the major groove of the DNA. Leucine zipper regulatory proteins typically include c-fos and c-jun (the AP1 transcription factor) that are important for normal development. Sequences of the bZIP domain can be obtained from public database, such as NCBI.

The winged helix domains are winged helix transcription factors consisting of 110 amino acids that have four helices and two-strand β-sheet. Exemplary families of winged helix domains are listed on the HMM library and genome assignment server.

The winged helix turn helix domains or wHTH consists of two wings, three a helices and three or four β-sheets (for detail, please see Ketan S Gajiwala and Stephen K Burley, Current Opinion in Structural Biology 2000, 10:110-116).

The DNA-recognition helix (third helix) binds to the major groove of DNA, and the wings usually bind to the minor groove or the backbone of DNA. The exemplary sequences of hydrophobic core of winged helix turn helix domains are shown in Gajiwala K S and Burley S K, Current Opinion in Structural Biology 2000, 10:110-116.

The HMG-box domains (High Mobility Group box) contains three irregular α helices separated by loops that are involved in DNA binding and regulate the DNA-dependent processes such as transcription, replication, and DNA repair, all of which require changing the conformation of chromatin. Sequences of the HMG-box domains can be obtained from public database, such as NCBI.

The Wor3 (White-Opaque Regulator 3) domains bind to specific DNA sequence. For detail description, please see Lohse M B et al. PNAS (2013) 110 (19): 7660-5. Exemplary amino acid sequence of Wor3 is GenBank Accession No. Q5A6T8.

The B3 domain is a highly conserved domain exclusively in transcription factors from higher plants and is approximately 100-120 residues. The B3 domain comprises seven β-sheets and two α-helices that form a pseudo-barrel protein fold. Proteins containing B3 domains are found in higher plants and include auxin response factors (ARFs), abscisic acid insensitive 3 (ABI3) and related to ABI3/VP1 (RAV). Sequences of the HMG-box domains can be obtained from public database, such as NCBI.

In one example, the site-specific DNA binding domain is GAL4 (SEQ ID NO: 7). The DNA sequence recognized by GAL 4 is 5×UAS (SEQ ID NO: 9).

"Percent (%) sequence identity" with respect to a target protein is defined as the percentage of amino acid residues in a sequence of interest that are identical with the amino acid residues in the target protein, after aligning the sequences and introducing gaps, if necessary, to achieve the maximum percent sequence identity, and not considering any conservative amino acid substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. See, for example, Altschul et al., Nucleic Acids Res. 25:3389-3402 (1997); Altschul et al., Methods in Enzymology 266: 460-480 (1996). Those skilled in the art can determine appropriate parameters for measuring alignment, including any algorithms needed to achieve maximal alignment over the full length of the sequences being compared.

In certain embodiments, the site-specific nuclease domain contains a DNA binding domain that is in the same type as the sequence-specific DNA binding domain. For example, a composition as disclosed herein contains a site-specific nuclease domain consisting of a TALEN and a sequence-specific DNA binding domain consisting of a TALE. In such case, the TALEN is engineered to recognize a target sequence in which a transgene is to be inserted while the TALE is engineered to recognize a sequence in the donor vector.

In certain embodiments, the DNA-binding domain contained in the site-specific nuclease domain is a different type from the sequence-specific DNA binding domain. For example, a composition disclosed herein contains a site-specific nuclease domain consisting of a ZFN and a sequence-specific DNA binding domain consisting of a TALE.

In preferred embodiments, the sequence recognized by the site-specific nuclease domain is different from the sequence recognized by the sequence-specific DNA binding domain. For example, a composition disclosed herein contains a site-specific nuclease domain consisting of a TALEN that recognizes a first nucleotide sequence and a sequence-specific DNA binding domain consisting of a TALE that recognizes a second nucleotide sequence, wherein the first nucleotide sequence is different from the second nucleotide sequence.

The site-specific nuclease domain is operably linked to the sequence-specific DNA binding domain via covalent bond, non-covalent interactions or through a linker. Thus, the site-specific nuclease domain and the sequence-specific DNA binding domain can be made separately and associate together through a covalent bond or non-covalent interactions. In certain embodiments, the composition is prepared by mixing the site-specific nuclease domain and the sequence-specific DNA binding domain. In preferred embodiments, the composition is a fusion protein produced through recombinant technology. In such cases, the site-specific nuclease domain can be linked to the N-terminus or C-terminus of the sequence-specific DNA binding domain.

In certain embodiments, the site-specific nuclease domain is linked to the sequence-specific DNA binding domain through a linker. The linker described herein refers to a peptide sequence designed to connect (e.g., join, link) two protein sequences, wherein the linker peptide sequence is typically not disposed between the two protein sequences in nature. Generally, linked proteins are contiguous or adjacent to one another and retain their respective operability and function when joined. Peptides comprising the chimeric polypeptides disclosed herein are linked by means of an interposed peptide linker comprising one or more amino acids. Such linkers may provide desirable flexibility to permit the desired expression, activity and/or conformational positioning of the chimeric polypeptide. A typical amino acid linker is generally designed to be flexible or to interpose a structure, such as an alpha-helix, between the two protein moieties. The linker peptide sequence can be of any appropriate length to connect one or more proteins of interest and is preferably designed to be sufficiently flexible so as to allow the proper folding and/or function and/or activity of one or both of the peptides it connects. In a polypeptide composition comprising a linker, the 5' end (e.g., terminus) of the linker peptide sequence (e.g., amino acid sequence) is adjacent to and covalently linked to the 3' end of one protein sequence (e.g., full-length protein or protein domain, fragment or variant) and, further, the 3' end of the linker amino acid sequence is adjacent to and covalently linked to the 5' end of another protein sequence. Polypeptide compositions produced in this manner are commonly referred to a fusion or chimeric protein/polypeptides and typically are made by the expression (e.g., transcription, translation) of nucleic acid sequences encoding the polypeptide compositions, in the appropriate system. Means by which to make fusion and/or chimeric polypeptides are well-known in the art (see for example, Sambrook et al., Molecular Cloning: A Laboratory Manual, Cold Springs Harbor Laboratory, 1992) New York which is incorporated by reference herein in its entirety). The foregoing peptide linkers can be flanked by one or more amino acid sequences that are encoded by a desired restriction endonuclease site or sites. Numerous endonuclease cleavage sites (e.g., EcoRI, BamHI, HindIII, AscI sites and the like) are well-known in the art, and the selection of which cleavage sites to include in the linker (and/or polypeptide) nucleic acid sequence is best determined by the skilled artisan, the site generally being chosen with regard to the respective nucleic acid sequences being linked. The endonuclease restriction sites can be the same site on each end of the linker sequence or different restriction sites as needed and/or desired.

Donor Vector

In certain embodiments, the composition further comprises a donor vector. The donor vector contains the DNA sequence that is recognized by the sequence-specific DNA binding domain. The donor vector also contains a replacement DNA sequence (e.g., a transgene) to be inserted to the target DNA sequence. Preferably, the donor vector also contains sequences that are necessary for homologous recombination, i.e., sequences homologous to the target DNA sequence and its vicinity sequences.

As used herein, a "replacement DNA sequence" refers to any nucleotide sequence to be inserted into a target DNA sequence, e.g., through homologous recombination. In certain embodiments, a replacement DNA sequence is a nucleotide sequence or a fragment thereof encoding a polypeptide. In certain embodiments, a replacement DNA sequence is a non-coding nucleotide sequence. In preferred embodiments, a replacement DNA sequence contains sequences facilitating homologous recombination, e.g., homologous arms.

In another aspect, the present disclosure provides a composition comprising one or more vectors. The vectors contain a first polynucleotide encoding (1) a fusion protein comprising a site-specific nuclease domain capable of cleaving a target DNA sequence; and (2) a sequence-specific DNA binding domain capable of specifically binding to a specific DNA sequence in a donor construct.

In another aspect, the present disclosure provides a cell that contains the composition disclosed above.

Method of Using Sequence-Specific Nuclease Composition

In another aspect, the present disclosure provides a method of inserting a replacement DNA sequence into a target DNA sequence of a cell. In certain embodiments, the method comprises introducing to the cell a composition a first polynucleotide encoding a fusion protein comprising a site-specific nuclease domain capable of cleaving the target DNA sequence, and a sequence-specific DNA-binding domain capable of specifically binding to a specific DNA sequence (recognition DNA sequence); and a donor vector comprising the recognition DNA sequence and the replacement DNA sequence.

Conventional viral and non-viral based gene transfer methods can be used to introduce the vectors into the target cells. Such methods can be used to administer nucleic acids encoding components of the composition to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome, protein complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bihm (eds) (1995); and Yu et al., Gene Therapy 1:13-26 (1994).

Methods of non-viral delivery of nucleic acids include lipofection, nucleofection, electroporation, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (in vivo). Conventional viral based systems could include retroviral, lentiviral, adenoviral, adeno-associated and herpes simplex viral vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

Example 1

The following is an example of a knock-in system with increased efficiency for homologous recombination.

The schematic of the knock-in system is illustrated in FIG. 1. Referring to FIG. 1, a sequence-specific nuclease composition includes a Cas9-DBD fusion protein and a donor vector containing a DBD recognition sequence. The Cas9 domain, in the guidance of a gRNA, cleaves the target site, while the DBD brings the donor vector to the vicinity of the target site. The gene of interest then inserts to the target site through recombination with increased efficiency.

Figure 2:
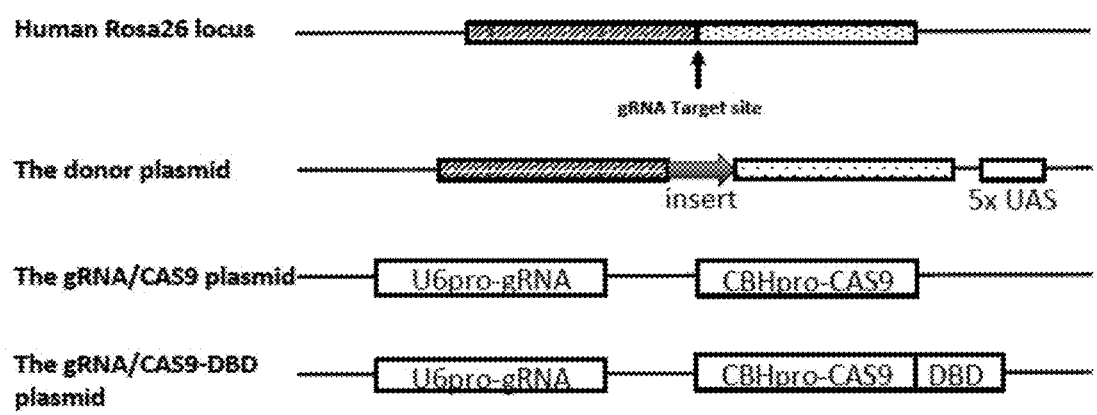
FIG. 2 illustrates the components of a knock-in system depicted in FIG. 1. The target site is located in the human ROSA26 locus, based on which a gRNA is designed. The donor plasmid includes an insert sequence flanked by homologous arms consisted of sequences surrounding the target site in the ROSA 26 locus. The donor plasmid also contains 5×UAS (Upstream Activating Sequence), which is recognized by GAL4 protein. The gRNA/Cas9-DBD plasmid contains a sequence encoding gRNA driven by U6 promoter and a Cas9-DBD fusion gene controlled by CBH promoter. As a control, the gRNA/Cas9 plasmid contains the sequence encoding gRNA driven by U6 promoter and a Cas9 gene controlled by CBH promoter.

FIG. 2 illustrates the components of the knock-in system. The target site is located in the human ROSA26 locus, based on which a gRNA was designed (SEQ ID NO: 10). The donor plasmid was designed to introduce a 60 bp insertion (arrow, SEQ ID NO: 11) flanked by two homology arms of the human ROSA26 locus (5' and 3' arms, SEQ ID NOs: 12 and 13). The donor plasmid also contained a Gal4 recognition sequence 5×UAS (SEQ ID NO: 9), which was cloned outside of the homology arms. pX459 plasmid (Addgene, SEQ ID NO: 16) was used for cloning hROSA26 gRNA together with either CAS9 or CAS9-Gal4 DNA binding domain (DBD).

The donor plasmid together with CAS9 or CAS9-DBD plasmids were transfected to HEK293 cells. One week after transfection, the genomic DNA was extracted and amplified by PCR with a pair of junction primer (SEQ ID NOs: 17 and 18). The PCR product was used for deep sequencing analysis. Around 3000 reads were obtained for each reaction. The HDR efficiency was calculated by the total number of the reads with perfect insertion over total number of reads. The final percentage reflecting the average of three experiments is illustrated in FIG. 3.

Figure 3:
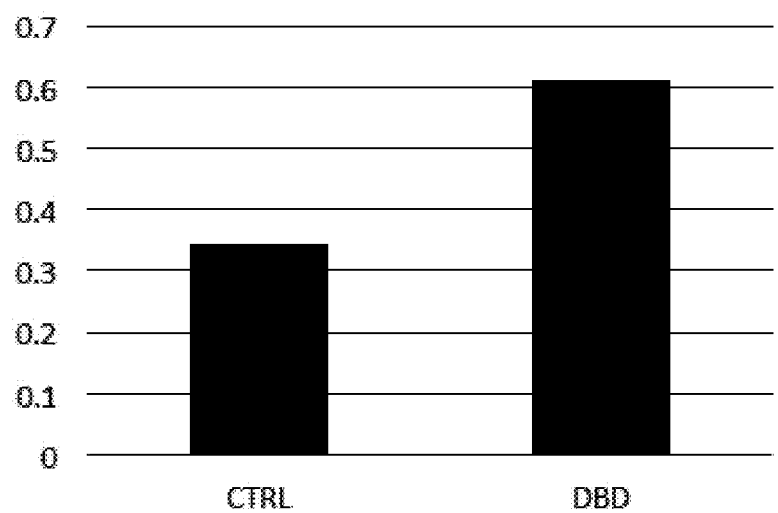
FIG. 3 illustrates the increased knock-in efficiency of CAS9-DBD fusion protein depicted in FIG. 2.

As illustrated in FIG. 3, the knock-in system using CAS9-DBD fusion protein and paired donor plasmid nearly doubled the efficiency of homologous recombination.

What is claimed is:

1. A composition for inserting a nucleotide sequence into a target DNA in a cell, said composition comprising:
   (a) a fusion protein or a polynucleotide encoding the same, said fusion protein comprising
      (i) a CRISPR-associated (Cas) nuclease capable of cleaving a target DNA sequence in a cell, and
      (ii) a sequence-specific DNA binding domain operably linked to the Cas nuclease and capable of specifically binding to a recognition DNA sequence; and
   (b) a donor vector comprising the recognition DNA sequence and a replacement DNA sequence,
   wherein the composition, when introduced into the cell, enhances insertion of the replacement DNA sequence in the target DNA sequence,
   wherein the target DNA sequence is located in the nucleus or cytoplasm of the cell,
   wherein the sequence-specific DNA binding domain is a Gal4 domain (SEQ ID NO: 7), and
   wherein the recognition DNA sequence is Gal4 recognition sequence 5×UAS (SEQ ID NO: 9).

2. The composition of claim 1, wherein the Cas nuclease is Cas9.

3. The composition of claim 1, further comprising a CRISPR-Cas guide RNA directed to the target DNA sequence.

4. A composition for inserting a nucleotide sequence into a target DNA in a cell, said composition comprising:
   (a) a first vector comprising a first polynucleotide encoding a fusion protein, said fusion protein comprising
      (i) a Cas nuclease capable of cleaving a target DNA sequence in a cell, and
      (ii) a sequence-specific DNA binding domain operably linked to the Cas nuclease and capable of specifically binding to a recognition DNA sequence; and
   (b) a donor vector comprising the recognition DNA sequence and a replacement DNA sequence,
   wherein the composition, when introduced into the cell, enhances insertion of the replacement DNA sequence in the target DNA sequence,
   wherein the target DNA sequence is located in the nucleus or cytoplasm of the cell,
   wherein the sequence-specific DNA binding domain is a Gal4 domain (SEQ ID NO: 7), and
   wherein the recognition DNA sequence is Gal4 recognition sequence 5×UAS (SEQ ID NO: 9).

5. The composition of claim 4, wherein the Cas nuclease is Cas9.

6. The composition of claim 5, further comprising a second vector comprising a second polynucleotide encoding a CRISPR-Cas guide RNA directed to the target DNA sequence, wherein the first vector and the second vector is the same or different.

7. A method for inserting a replacement DNA sequence into a target DNA sequence of a cell comprising:
  introducing into the cell a composition comprising
    (a) a first polynucleotide encoding a fusion protein, said fusion protein comprising
      (i) a Cas nuclease capable of cleaving the target DNA sequence, and
      (ii) a sequence-specific DNA-binding domain operably linked to the Cas nuclease and capable of specifically binding to a recognition DNA sequence; and
    (b) a donor vector comprising the recognition DNA sequence and the replacement DNA sequence,
  wherein the target DNA sequence is located in the nucleus or cytoplasm of the cell,
  wherein the sequence-specific DNA binding domain is a Gal4 domain (SEQ ID NO: 7), and
  wherein the recognition DNA sequence is Gal4 recognition sequence 5×UAS (SEQ ID NO: 9).

8. The method of claim 7, wherein the Cas nuclease is Cas9.

9. The method of claim 8, further comprising introducing into the cell second polynucleotide encoding a CRISPR-Cas guide RNA directed to the target DNA sequence, wherein the first polynucleotide and the second polynucleotide are included in one or more vectors.

* * * * *